(12) United States Patent
Trkovnik et al.

(10) Patent No.: US 10,266,545 B2
(45) Date of Patent: Apr. 23, 2019

(54) COUMARIN DERIVATIVE AS ANTIVIRAL AGENT, PHARMACEUTICAL COMPOSITION THEREOF, ITS PREPARATION AND USE

(71) Applicant: I-NOVA MEDICINSKA ISTRAZIVANJA D.O.O., Vukovar (HR)

(72) Inventors: Mladen Trkovnik, Zagreb (HR); Milan Cacic, Vukovar (HR); Jonuz Rizvani, Zagreb (HR)

(73) Assignee: I-NOVA MEDICINSKA ISTRAZIVANJA D.O.O., Vukovar (HR)

( * ) Notice: Subject to any disclaimer, the term of this patent is extended or adjusted under 35 U.S.C. 154(b) by 0 days.

(21) Appl. No.: 15/562,081

(22) PCT Filed: Feb. 2, 2016

(86) PCT No.: PCT/HR2016/000005
§ 371 (c)(1),
(2) Date: Sep. 27, 2017

(87) PCT Pub. No.: WO2016/156888
PCT Pub. Date: Oct. 6, 2016

(65) Prior Publication Data
US 2018/0072752 A1    Mar. 15, 2018

(30) Foreign Application Priority Data

Feb. 2, 2016    (WO) ............... PCT/HR2016/000005

(51) Int. Cl.
*C07D 311/18*    (2006.01)
*C07D 493/04*    (2006.01)
*C07D 407/14*    (2006.01)

(52) U.S. Cl.
CPC .......... *C07D 493/04* (2013.01); *C07D 311/18* (2013.01); *C07D 407/14* (2013.01)

(58) Field of Classification Search
None
See application file for complete search history.

(56) References Cited

U.S. PATENT DOCUMENTS 7,384,975 B2 *    6/2008    Mercep ................ C07D 493/04
514/453

FOREIGN PATENT DOCUMENTS

| WO | 03029237 A1 | 4/2003 |
| WO | 2005010007 A1 | 2/2005 |
| WO | 2005095411 A1 | 10/2005 |

OTHER PUBLICATIONS

Borges et al., Simple Coumarins and Analogues in Medicinal Chemistry: Occurrence, Synthesis and Biological Activity, Current Current Medicinal Chemistry, 2005, pp. 887-916.
Excerpts from Encyclopedia of Pharmaceutical Technology, Third Edition, by Informa Healthcare USA, Inc., 2007, 75 pages.
Kostova, Coumarins as Inhibitors of HIV Reverse Transcriptase, Current HIV Research, 2006, pp. 347-363.
Montefiori et al., Evaluation of Antiviral Drugs and Neutralizing Antibodies to Human Immunodeficiency Virus by a Rapid and Sensitive Microtiter Infection Assay, Journal of Clinical Microbiology, Feb. 1988, vol. 26, No. 2, pp. 231-235.
Mosmann, Rapid colorimetric assay for cellular growth and survival: application to proliferation and cytotoxicity assays, J. Immunol Methods, Dec. 16, 1983;65(1-2); Abstract.
Shao et al., A non-radioactive microtitre plate reverse transcriptase (RT) assay, based on immobilized template, for screening of RT activity inhibitors and evaluation of their mode of action, Antiviral Chemistry & Chemotherapy 1997 8(2), pp. 149-159.
International Search Report issued in PCT/HR2016/000005 dated Apr. 22, 2016, 4 pages.
Written Opinion of the International Search Authority issued in PCT/HR2016/000005 dated Apr. 22, 2016, 5 pages.
International Search Report and Written Opinion issued in PCT Application No. PCT/HR2015/000008, dated Jun. 9, 2015, 9 pages.

* cited by examiner

*Primary Examiner* — Samantha L Shterengarts
(74) *Attorney, Agent, or Firm* — RatnerPrestia

(57) ABSTRACT

The present invention discloses the novel coumarin derivative of formula (1):

its synthesis, pharmaceutical composition, preparation and use thereof. The pharmaceutical composition including: (1) the novel coumarin derivative of formula (1) as active pharmaceutical ingredient; and (2) one or more pharmaceutical excipients, required to yield final dosage forms suitable for therapeutic administration. The composition is safe and efficient therapeutic agent for viral diseases including the acquired immunodeficiency syndrome (AIDS).

15 Claims, 2 Drawing Sheets

Cytotoxic activity of 7,9-dihydroxy-3-(4,5,7-trihydroxy-2-oxo-2H-chromene-3-yl)-4H-furo[3,2-c]chromen-4-one (1) on the viability of model MT-4 cell line at 72 h Cytotoxic activity of 7,8-dihydroxy-3-(4,6,7-trihydroxy-2-oxo-2H-chromen-3-yl)-4H-furo[3,2-c]chromen-4-one (2) on the viability of model MT-4 cell line at 72 h

COUMARIN DERIVATIVE AS ANTIVIRAL AGENT, PHARMACEUTICAL COMPOSITION THEREOF, ITS PREPARATION AND USE

TECHNICAL FIELD

The invention relates to a novel antiviral coumarin derivative 7,9-dihydroxy-3-(4,5,7-trihydroxy-2-oxo-2H-chromene-3-yl)-4H-furo[3,2-c]chromen-4-one (1), its synthesis, a new pharmaceutical composition based on 1, its preparation and use.

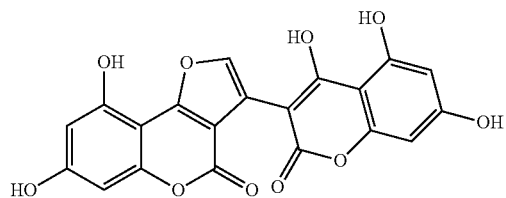

1

TECHNICAL PROBLEM

Technical problem is related to safe and efficient therapy for treatment of viral infections and various virus-causing diseases, including the acquired immunodeficiency syndrome (AIDS) caused by the human immunodeficiency virus type-1 (HIV-1), with effective medicament based on more efficient pharmaceutical active ingredient (API).

The technical problem that is solved by the present invention is based on a novel compound 1 and its use, in the form of various pharmaceutical final dosage forms, in the treatment of viral diseases including the HIV-1.

PREVIOUS STATE OF ART

Coumarin derivatives are well known pool of numerous valuable compounds of various pharmacological activities, for instance see literature reference 1:

1) F. Borges, F. Roleira, N. Milhazes, L. Santana, E. Uriarte: Simple Coumarins and Analogues in Medicinal Chemistry: Occurence, Synthesis and Biological Activity, *Curr. Med. Chem.* 12 (2005) 887-916.

4-Hydroxycoumarins undergo aldol-type condensation reaction with aldehydes yielding corresponding 1-hydroxyalkyl derivatives of parent aldehyde at 3-position of starting 4-hydroxycoumarin. This type of condensation products were already studied from both synthetic and pharmacological points of view.

The prior art to the present invention is disclosed in the following literature references:

2) M. Mercep, M. Mesic, B. Hrvacic, I. J. Elenkov, I. Malnar, S. Markovic, L. Simicic, A. Cempuh Klonkay: Substituted furochromenes, preparation thereof and their anti-inflammatory action, WO2005/010007A1, Pliva-Istrazivacki institut d.o.o.;

3) M. Mercep, M. Mesic, B. Hrvacic, I. J. Elenkov, I. Malnar: Furochromene derivative with anti-inflammatory activity, WO2005/095411A1, Pliva-Istrazivacki institut d.o.o.;

4) Z. Ivezic: [Synthesis of novel hydroxycoumarin derivatives as possible HIV-1 protease inhibitors (in Croatian)] Ph.D. Thesis (2000) Pliva Inc., Zagreb, Croatia; Faculty of Science, University of Zagreb, Croatia.

Mercep and co-workers in WO2005/010007A1; Pliva-Istrazivacki institut d.o.o.; disclosed condensation products of various 4-hydroxycoumarins with glyoxal yielding several compounds of general formula I of anti-inflammatory activity. Furthermore, in another application Mercep and co-workers described 2,7,9-trihydroxy-3-(4,5,7-trihydroxy-2-oxo-2H-chromene-3-yl)-2,3-dihydro-4H-furo[3,2-c]chromen-4-one (II) for which they also reported anti-inflammatory activity:

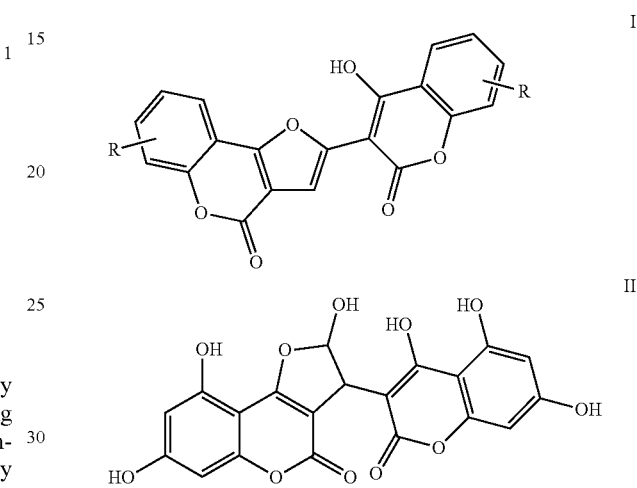

Additionally Ivezic disclosed several tetrakis-coumarin derivatives III of 4-hydroxycoumarin and various dialdehydes, as well as alkoxy-derivatives of corresponding bis-condensation products of general formula IV. The latter compounds were tested on antiviral activity including the anti-HIV activity:

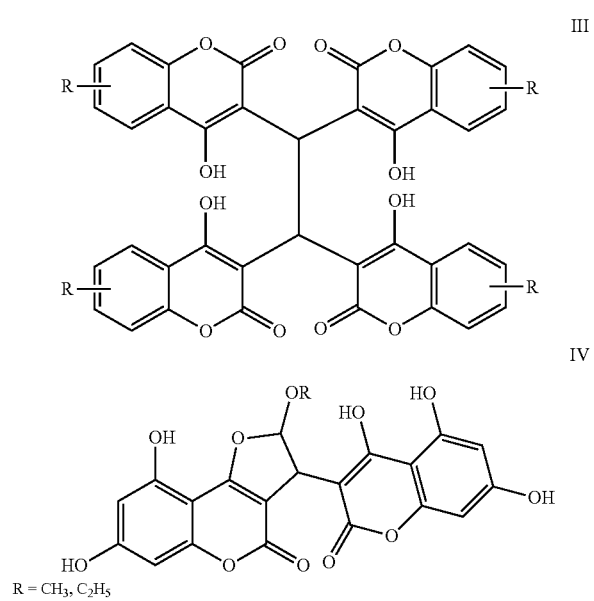

R = CH$_3$, C$_2$H$_5$

It is obvious to the person skilled in the art of pharmaceutical chemistry that compounds I-IV do not have much connection with the compound 1 from the present invention. The most similar compounds are II and IV which are the closest derivatives to compound 1, but compound II and compounds of general formula IV can establish more interactions with various enzyme active sites, e.g. at least one hydrogen-bond more than the compound 1 in the same situation; II as hydrogen-bond donor thanks to the hydrogen atom at 2-hydroxy-furane moiety, and IV as hydrogen-bond acceptor due to proton-accepting potential of oxygen atom of 2-alkoxy-furane moiety.

Thus, from standpoint of pharmaceutical chemistry and pharmacology, there exist significant structural differences between the known compounds II or IV versus compound 1 from the present invention.

Furthermore Kostova described several substituted coumarin derivatives with anti-HIV activity, see literature reference 5:

5) I. Kostova: Coumarins as Inhibitors of HIV Reverse Transcriptase, Curr. HIV Res. 4 (2006) 347-363.

However, none of these coumarins is not structural analogue of the compound 1 from the present invention.

CLOSEST PRIOR ART

It seems that the closest prior art to the present invention is disclosed in the patent application of Z. Ivezic and M. Trkovnik, wherein 7,8-dihydroxy-3-(4,6,7-trihydroxy-2-oxo-2H-chromen-3-yl)-4H-furo[3,2-c]chromen-4-one (2) and its antiviral activity were described, see literature reference 6:

6) Z. Ivezic, M. Trkovnik: Products of condensations of hydroxycoumarin derivatives with aromatic and aliphatic dialdehydes, their preparation and antiviral action thereof, WO 03/029237 A1, Pliva d.d., Zagreb, Croatia.

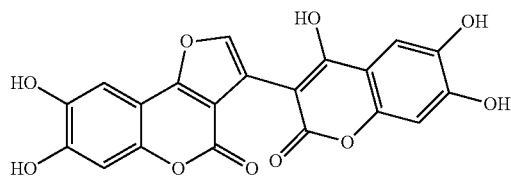

The above cited compound 2 is used herein as the control compound.

According to our best knowledge, the coumarin derivative 7,9-dihydroxy-3-(4,5,7-trihydroxy-2-oxo-2H-chromene-3-yl)-4H-furo[3,2-c]chromen-4-one (1) that is synthesized in our laboratory, its various pharmaceutical final dosage forms, and pharmacological activity as therapeutic agent for treatment of either viral or, specifically, immunodeficiency virus type-1 (HIV-1) infections, has not been disclosed in the form of patent or non-patent literature.

SUMMARY OF THE INVENTION

The present invention discloses the new coumarin derivative 7,9-dihydroxy-3-(4,5,7-trihydroxy-2-oxo-2H-chromene-3-yl)-4H-furo[3,2-c]chromen-4-one (1), its synthesis, pharmaceutical composition based on 1, its preparation and use.

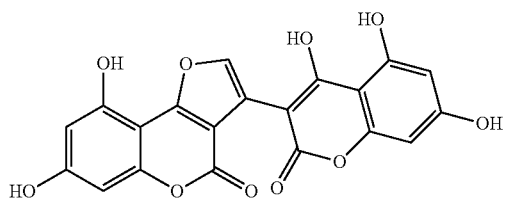

In another embodiment, the present invention discloses the pharmaceutical composition consisting of:
(1) 7,9-dihydroxy-3-(4,5,7-trihydroxy-2-oxo-2H-chromene-3-yl)-4H-furo[3,2-c]chromen-4-one (1) or a pharmaceutically acceptable salt or hydrate thereof as active pharmaceutical ingredient; and
(2) one or more pharmaceutical excipients, required to yield final dosage forms suitable for therapeutic administration.

The composition is safe and efficient therapeutic agent for treatment of viral infections and virus-causing diseases including the acquired immunodeficiency syndrome (AIDS).

DETAILED DESCRIPTION

Figure 1:
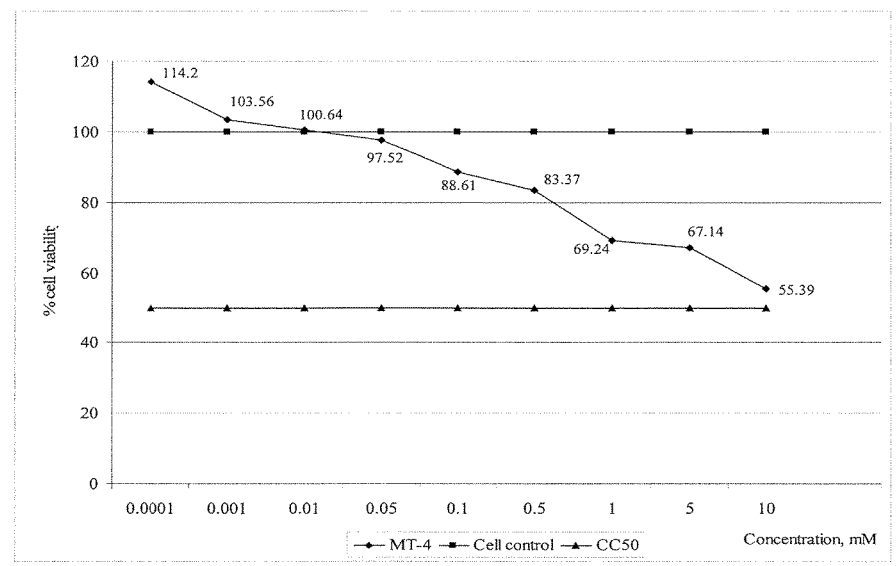
FIG. 1—Cytotoxic activity of 7,9-dihydroxy-3-(4,5,7-trihydroxy-2-oxo-2H-chromene-3-yl)-4H-furo[3,2-c]chromen-4-one (1) on viability of model MT-4 cell line. Dose - response curves obtained after 72 h culturing.

The present invention discloses the new coumarin derivative 7,9-dihydroxy-3-(4,5,7-trihydroxy-2-oxo-2H-chromene-3-yl)-4H-furo[3,2-c]chromen-4-one (1), its synthesis, pharmaceutical composition, preparation, and use thereof.

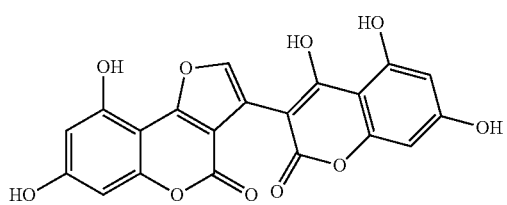

On the basis of new compound 1 the present invention discloses pharmaceutical composition comprising:
(1) 7,9-dihydroxy-3-(4,5,7-trihydroxy-2-oxo-2H-chromene-3-yl)-4H-furo[3,2-c]chromen-4-one (1) or a pharmaceutically acceptable salt or hydrate thereof as active pharmaceutical ingredient; and
(2) one or more pharmaceutical excipients, required to yield final dosage forms suitable for therapeutic administration.

The composition is safe and efficient therapeutic agent for viral infections and virus-causing diseases including the acquired immunodeficiency syndrome (AIDS) caused by human immunodeficiency virus type 1 (HIV-1), type 2 (HIV-2) and their subtypes.

The composition of the present invention can be in various final dosage forms that are selected by the manner of use and include the following forms:
(1) oral: tablets, capsules, granules, powder, divided powder, effervescent tablets, oral solution, oral suspension, syrup, lozenges, chewing gum;
(2) topical: ointment, cream, gel, liniment, lotion, poultice, therapeutic patch;
(3) parenteral: injection solution;
(4) vaginal: irrigating solution, gel, tablet, vaginal suppository;
(5) rectal: rectal suppository;
(6) ophthalmical: eye drops, eye ointment, eye wash;
(7) nasal: nasal drops, nasal spray, nasal ointment, nasal wash;
(8) otic: ear drops; and
(9) inhalation: spray solution or suspension; as well as all other commonly used pharmaceutical final dosage forms because compound 1 can be readily formulated in many different dosage forms.

The pharmaceutical excipients required to prepare final dosage forms, as described above, are one or more substances selected from the group comprising:
(1) fillers; for solid dosage forms like tablets, capsules, powders, suppositories, etc.;
(2) diluents; for liquid dosage forms such as syrup, liniment, lotion, nasal drops, eye drops, etc.;
(3) emollients; for topical dosage forms like creams, ointments, etc.;
(4) emulsifiers;
(5) binders;
(6) disintegrants;
(7) lubricants;
(8) humectants;
(9) thickeners;
(10) chelating agents;
(11) preservatives; this are used optionally, depending on container-closure system used on packaging;
(12) antioxidants; as well as all other classes of excipients that are commonly used in the pharmaceutical technology.

Filler is one or more substances selected from the group comprising: microcrystalline cellulose, lactose, saccharose, inulin, mannitol, sorbitol, maltitol, xylitol, dextrin, maltodextrin, starch, calcium carbonate, mixtures of these substances, or other pharmaceutically acceptable fillers.

Fillers in dosage forms like suppositories are selected from the group comprising: glycerol; soaps like sodium stearate; hydrogenated coconut oils like Witepsol H15; coconut oil; natural waxes like beeswax or candelilla wax; mineral wax like paraffin; synthetic waxes like castor wax or solid polyethyleneglycols (PEG); mixtures of these substances, or other pharmaceutically acceptable fillers.

Diluent is one or more substances selected from the group comprising: purified water; ethanol; medicinal wines; 1,2-propylene glycol; glycerol; polyethyleneglycols (PEG) like PEG 400; plant oils like sunflower oil, sesame oil, or medium-chain triglycerides; mutually miscible or emulsifiable mixtures of these substances, or other pharmaceutically acceptable diluents.

Purified water that is used as the diluents in the composition of the present invention meets the requirements of European pharmacopoeia 8.0, p. 3561-3562 for pharmaceutical water.

Emollient is one or more substances selected from the group comprising: petroleum jelly; mineral oil; plant oils like almond, sunflower, or sesame oil; medium-chain triglycerides; natural or synthetic esters of monovalent alcohols with higher fatty acids like isopropyl myristate, jojoba oil, or beeswax; silicone oil; higher fatty acids like stearic acid; higher fatty alcohols like cetyl alcohol; mixtures of these substances, or other pharmaceutically acceptable emollients.

Emulsifier is one or more substances selected from the group comprising: lanolin; ethoxylated lanolin; lanolin alcohols; ethoxylated lanolin alcohols; lecithin; hydrogenated lecithin; mono- and diesters of glycerol with higher fatty acids like glyceryl monostearate; sorbitan esters with higher fatty acids such as sorbitan monostearate; ethoxylated higher fatty alcohols or acids like polyoxyethylene(23) laurylether or polyoxyethylene(2) oleate, wherein numbers 23 and 2 represents the number of ethyleneglycol units; esters of ethoxylated sorbitan like polysorbate 60; water soluble soaps like sodium stearate; mixtures of these substances, or other pharmaceutically acceptable emulsifiers.

Binder is one or more substances selected from the group comprising: glucose syrup; glucose-fructose syrup; honey; saccharose; lactose; gelatine; sorbitol; maltitol; xylitol; cellulose gums like hydroxypropyl methylcellulose (HPMC), hydroxypropyl cellulose (HPC), hydroxyethyl cellulose (HEC), methyl cellulose (MC), sodium carboxymethyl cellulose (NaCMC); synthetic polymers such as polyvinyl alcohol (PVA), polyacrylic acid (PAA) and its copolymers, polyvinylpyrrolidone (PVP); hyaluronic acid; various gums like gum arabic, xanthan gum, tragacanth; alginic acid and its salts like sodium alginate; mixtures of these substances, or other pharmaceutically acceptable binders.

Disintegrant is one or more substances selected from the group comprising: crosslinked polyvinylpyrrolidone (PVP); sodium starch glycolate; crosslinked sodium carboxymethylcellulose (NaCMC); modified starches; mixtures of these substances, or other pharmaceutically acceptable disintegrants.

Lubricant is one or more substances selected from the group comprising: magnesium, calcium, aluminium, and zinc soaps, e.g. magnesium stearate; higher fatty acids like stearic acid; talc; colloidal silica (silicon dioxide); mixtures of these substances, or other pharmaceutically acceptable lubricants.

In ophthalmic water-based final dosage forms, lubricant is selected from the group comprising: hydroxypropyl methylcellulose (HPMC); hydroxypropyl cellulose (HPC); hydroxyethyl cellulose (HEC); methyl cellulose (MC); sodium carboxymethyl cellulose (NaCMC); polyvinyl alcohol (PVA); polyacrylic acid (PAA) and its copolymers; hyaluronic acid; polyvinylpyrrolidone (PVP); glycerol; 1,2-propylene glycol; trehalose; polyethylene glycols (PEG) like PEG 400; mixtures of these substances, or other pharmaceutically acceptable ophthalmic lubricants.

Humectant is one or more substances selected from the group comprising: glycerol; 1,2-propylene glycol; hexylene glycol; liquid sorbitol; d-panthenol; polyethylene glycols; other commonly known pharmaceutically acceptable humectants, or their mixtures.

Thickener is one or more substances selected from the group comprising: cellulose gums like hydroxypropyl methylcellulose (HPMC), hydroxypropyl cellulose (HPC), hydroxyethyl cellulose (HEC), methyl cellulose (MC), sodium carboxymethyl cellulose (NaCMC); synthetic polymers such as polyvinyl alcohol (PVA), polyacrylic acid (PAA) and its copolymers, polyvinylpyrrolidone (PVP); various gums like gum arabic, xanthan gum, tragacanth; alginic acid and its salts like sodium alginate; mixtures of these substances, or other pharmaceutically acceptable thickeners.

Chelating agent is one or more substances selected from the group comprising: sodium, or potassium salts of ethylenediaminetetraacetic (edetic) acid (EDTA); diethylenetriamine pentaacetic acid (DTPA); nitrilotriacetic acid (NTA); water soluble citrate salts like trisodium citrate dihydrate; mixtures of these substances, or other pharmaceutically acceptable chelating agents. Representative example of such chelating agents is disodium edetate dihydrate ($Na_2EDTA.2H_2O$).

Preservative is one or more substances selected from the group comprising: parabens like methyl 4-hydroxybenzoate, ethyl 4-hydroxybenzoate, propyl 4-hydroxybenzoate, butyl 4-hydroxybenzoate; 4-chloro-m-cresol; triclosan; chlorobutanol; chlorhexidine and its salts; quaternary ammonium salts such as benzalkonium chloride or cetrimonium bromide; benzoic acid; sorbic acid; benzyl alcohol; 2-phenoxyethanol; dehydroacetic acid (3-acetyl-2-hydroxy-6-methyl-4H-pyran-4-one); mixtures of these substances, or other pharmaceutically acceptable preservatives.

Antioxidant is one or more substances selected from the group comprising: ascorbic acid, its salts and esters like calcium ascorbate or ascorbyl palmitate; 2,6-di-tert-butyl-4-methylphenol (BHT); tert-butyl-anisole (BHA); propyl gallate; α-tocopherol and its esters like α-tocopheryl acetate; rosemary (*Rosmarinus officinalis*) extract; mixtures of these substances, or other pharmaceutically acceptable antioxidants.

Synthesis of 7,9-dihydroxy-3-(4,5,7-trihydroxy-2-oxo-2H-chromene-3-yl)-4H-furo[3,2-c]chromen-4-one (1)

The synthesis of compound 1 was performed by the Pechmann condensation of phloroglucinol (3) and cyanoacetic acid (4) in the presence of gaseous hydrogen chloride (HCl) as catalyst in refluxing diethyl ether as reaction solvent (step I).

Thus obtained intermediate ketimide 5 was separated after work-up of the reaction mixture and hydrolyzed by refluxing in concentrated hydrochlorid acid (HCl) furnishing 4,5,7-trihydroxy-2H-chromen-2-one (6) (step II). Also, the compound 6 is commercially available product.

Coumarin derivative 6 was subjected into condensation with glyoxal (7) in refluxing acetone (56° C.) yielding compound 1 in an aldol-type condensation (step III).

The preparation of compound 1 in step III can be alternatively performed at temperatures between −20° C. to +100° C., e.g. in refluxing 1,4-dioxane.

Alternatively, the synthesis of both intermediate coumarin 6 (steps I and II), and compound 1 (step III) can be performed with other protic or Lewis acids that are known to those skilled in the art of organic and pharmaceutical chemistry.

Also, instead of these reaction solvents: diethylether in the I reaction step of Pechmann condensation; as well as acetone in the III reaction step of aldol-type condensation; other inert organic solvents like tetrahydrofuran (THF), 1,4-dioxan, diisopropylether, dichloromethane, can be used.

The synthesis of compound 1 is shown in Scheme 1.

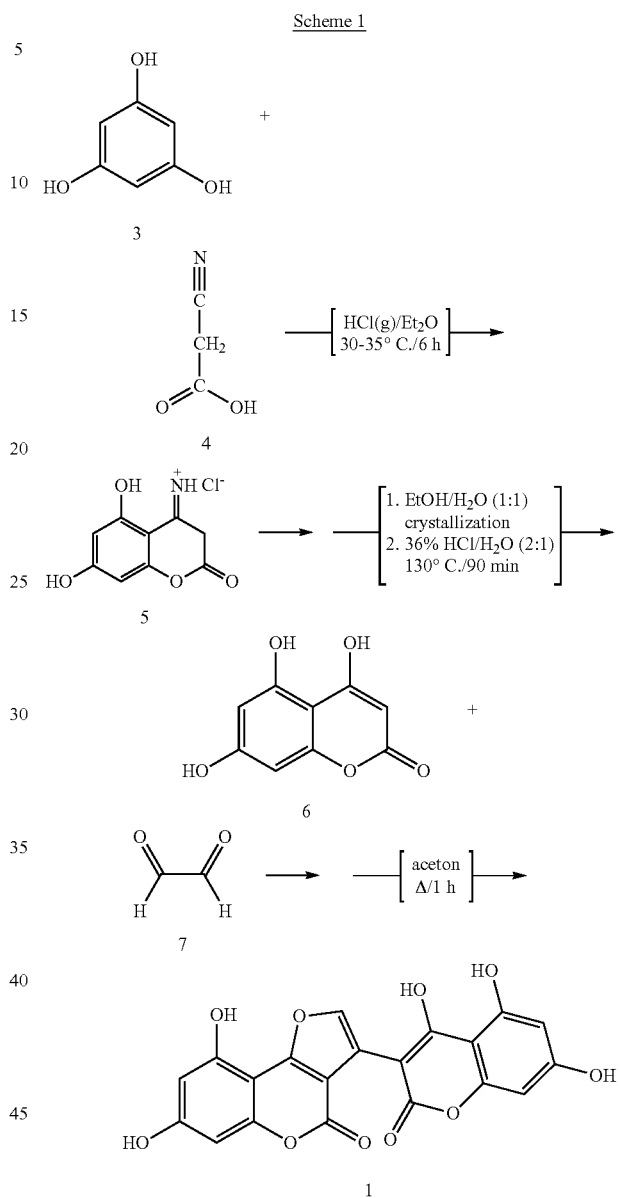

The procedure for synthesis of compound 1 and characterization data for intermediate 6 and final compound 1 are described in Example 1. Analytical methods for its qualitative (TLC), quantitative (HPLC), and determination and mass spectra (MS) analyses are described in Example 2.

Since free phenolic OH groups of the compound 1 do act as acids, the corresponding salts with pharmaceutically acceptable, non-toxic bases can be prepared. Such salts do have certain advantages over free acid 1 due to eventually increased water solubility.

Examples of useful bases that can be employed for preparation of various pharmaceutically acceptable salts of compound 1 are: sodium hydroxide (NaOH), potassium hydroxide (KOH), calcium hydroxide [$Ca(OH)_2$], magnesium hydroxide [$mg(OH)_2$], ammonium hydroxide ($NH_4OH$), tetramethyl/ethylammonium hydroxide [$R_4N^-$ $OH^-$; $R=CH_3$, $C_2H_5$], choline hydroxide [($CH_3)_3N$ (CH$_2$CH$_2$OH)OH], other pharmaceutically acceptable bases, or mixtures of these substances in various molar ratios.

These pharmaceutically acceptable salts of compound 1 can be prepared by reaction of 1 with above mentioned bases at −20° C. to +100° C. in an inert reaction solvent such as purified water, methanol, ethanol, isopropanol, other inert organic solvents, or mixtures of these substances.

Thus obtained solutions or suspensions of formed salts are converted to pure anhydrous or solvated or hydrated salts by crystallization, evaporation to dryness, or by lyophilisation, or other alternative common techniques known in the art of pharmaceutical chemistry.

Often such salts form various solvates or hydrates that can alternatively be employed as active pharmaceutical ingredient (API) of the composition of this invention.

The procedure for preparation of representative pharmaceutically acceptable monosodium salt of compound 1 is described in Example 3.

Preparation of the Composition from the Present Invention

The composition from the present invention involves all pharmaceutically useful final dosage forms as described above.

The technology of preparation of various final dosage forms are known to the person skilled in the art of pharmaceutical technology, see for instance literature reference 7:
7) J. Swarbrick, J. C. Boylan: Encyclopedia of pharmaceutical technology; New York, M. Dekker (1998-2001).

Final dosage form of powder is manufactured by homogenization of powderous ingredient 7,9-dihydroxy-3-(4,5,7-trihydroxy-2-oxo-2H-chromene-3-yl)-4H-furo[3,2-c]chromen-4-one (1) which serves as an active pharmaceutical ingredient (API) with one or more powderous excipients selected from the group comprising: filler, lubricant, and optionally, other pharmaceutical excipients.

Thus obtained powder can be granulated, by using one or more suitable diluents and binders, yielding dosage forms of granules. Diluents like purified water for wet granulation process are used on quantum satis (q.s.) principle.

Powders and granules can be compacted to give final dosage forms of tablets, or alternatively, filled into gelatin or various vegetable capsules furnishing final dosage form of capsules.

Liquid dosage forms such as oral solution, suspension, or syrup are prepared by dissolution of compound 1 in suitable diluent like purified water, or mixtures of purified water with humectants and thickeners. Liquid formulations based on predominantly water have to be preserved against microbiological spoilage by addition of suitable preservative.

Topical dosage form of ointment is prepared by homogenization of fine powderous compound 1 into the hydrophilic or lipophilic ointment base. The former are, for instance, a mixture of solid and liquid polyethylene glycols (PEG), whilst the latter are various mixtures of waxes, plant oils, lanolin, etc.

Creams and lotions from the class of water-in-oil (W-O) or oil-in-water (O-W) emulsions are prepared by homogenization of compound 1 in the corresponding base emulsions.

There can be many other preparation technologies of the composition of the present invention in all mentioned and other possible final dosage forms, what is known to the person skilled in the art of pharmaceutical technology.

For demonstration, typical final dosage forms of the composition from this invention are given in Examples 8-15.

Study of Cytotoxicity of 7,9-dihydroxy-3-(4,5,7-trihydroxy-2-oxo-2H-chromene-3-yl)-4H-furo[3,2-c]chromen-4-one (1) via Determination of Maximal Non-Toxic Concentration (MNC) and Cytotoxic Concentration (CC$_{50}$) and Comparison with Literature Analogue 2

Cytotoxicity of compound 1 was determined through the study of cell growth and viability by the methods of determination of maximal non-toxic concentration (MNC) and concentration required for cell viability by 50% (CC$_{50}$). Maximal non-toxic concentration (MNC) was defined as the highest concentration of the test substance, which does not cause injury or death of the treated cells. Cytotoxic concentration at 50% (CC$_{50}$) was defined as the concentration of the test substance at which 50% of the cells die as a result of toxicity of the test substance.

Evaluation of cytotoxicity was an important part of the assessment of antiviral activity of compound 1 since its beneficial antiviral effect should be selective for virus-specific processes with little or no effects on the metabolism of host cells. The study was performed with 7,8-dihydroxy-3-(4,6,7-trihydroxy-2-oxo-2H-chromen-3-yl)-4H-furo[3,2-c]chromen-4-one (2) as a control compound which was described in the literature reference 6.

The study of cytotoxicity of compounds 1 and 2 was performed on MT-4 cell line.

The MT-4 cell line was not infected with human immunodeficiency (HIV) virus and was used as a classical model for reproduction of acute infection with HIV-1, for the study of effects of various putative inhibitors of HIV-1, and for the titration of virus infectivity by cytopathic effect; see literature reference 8:
8) D. Montefiori, E. Robinson, Jr. Shirley, S. Schuffman, W. Mitchell: Evolution of antiviral drugs and neutralizing antibodies by rapid and sensitive microtiter infection assay, *J. Clin. Microbiol.* 26 (1998) 231-235.

Cell viability was estimated by a modification of the 3-(4,5-dimethylthiazol-2-yl)-2,5-diphenyltetrazolium bromide (MTT) assay, which is described in the literature reference 9:
9) T. Mosmann: Rapid colorimetric assay for cellular growth and survival: Application to proliferation and cytotoxicity assays, *J. Immunol. Methods* 65 (1983) 55-63.

Cell viability was reported as the percentage (%) of viable cells in the wells treated with different concentrations of the test compound 1, compared to the control cells untreated with the substance. Maximal non-toxic concentration (MNC) and cytotoxic concentration for 50% of cells (CC$_{50}$) were calculated from the constructed "dose—cellular survival" curve.

Both MNC and CC$_{50}$ values were evaluated simultaneously by morphological and by cell survival criteria. We used MTT-test, determining the living and early apoptotic cells. When microscopic observation of the morphology of the monolayer were carried out at 72 h after the treatment with test compound 1 and control compound 2 solutions in concentration range from 10 mM to 0.01 mM, typical cytopathology characterizing toxic effects were not registered. We found some morphology changes of cell line in comparison with the cell control only in treated wells with highest concentration of 100 mM, whose impact could be due to the content of a diluent used (DMSO).

To evaluate whether this effect is due to the toxicity of the tested substance 1, control compound 2, or DMSO, mortgaging control of growth medium RPMI 1640 supplemented with 2% FBS and DMSO was tested. We conducted a test with the same concentration range as the test compound 1 and control compound 2. The results show that the toxicity of DMSO in lower dilutions is extremely small and does not have a toxic effect on the cells of both lines.

Cytotoxic activity of compound 1 on viability of model MT-4 cell line can be seen from the dose - response curves obtained after 72 h culturing, see FIG. 1. Cytotoxic activity of control compound 2 on viability of model MT-4 cell line can be seen from the dose—response curves obtained after 72 h culturing, see FIG. 2.

The results of MNC and $CC_{55}$ obtained in the cell line for compounds 1 and 2 are given in Table 1. Detailed experimental procedure of cytotoxicity determination of compounds 1 and 2 is given in Example 4.

TABLE 1

Cytotoxic effect of 7,9-dihydroxy-3-(4,5,7-trihydroxy-2-oxo-2H-chromene-3-yl)-4H-furo[3,2-c]chromen-4-one (1) and control compound 2 on MT-4 cells at 72 h.

| No. | Compound | $MNC^a$ [mM] | $CC_{50}^b$ [mM] |
|---|---|---|---|
| | Closest State of the Art: | | |
| 1 | Control compound 2 | 0.01 | 10 |
| | This invention: | | |
| 2 | Compound 1 | 0.01 | 10 |

$^a$MNC = maximal non-toxic concentration.
$^b$CC$_{50}$ = cytotoxic concentration for 50% cells.

In conclusion, the results showed that both compound 1 and control compound 2 exhibit low and practically the same cytotoxicity against MT-4 cell line. These results were dose-dependent.

We concluded that these results strongly support the initial hypothesis that compound 1 is essentially non-toxic, and thus can be safely used as pharmaceutical active substance (API). Of course, further toxicological studies have to be performed, but this is obviously not essential for demonstration of novelty and inventive step of this invention.

Study of antiviral activity of 7,9-dihydroxy-3-(4,5,7-trihydroxy-2-oxo-2H-chromene-3-yl)-4H-furo[3,2-c]chromen-4-one (1) and comparison with literature analogue 2

The first study of antiviral activity of compound 1 and the control compound 2 was performed on example of its influence on replication of human immunodeficiency virus 1 (HIV-1) by microtiter infectivity assay in cell culture and by evaluation of concentration of compound 1 or 2, which inhibits virus replication by 50% ($IC_{50}$) as well as by selectivity index (SI).

The cell line used in this study was also the MT-4 cell line as described above.

A microplate assay of infectivity in cell culture, based on consideration of a cytopathic effect of the virus was described in the literature, see reference 8. At least 4 different concentrations: 10×MNC, $MNC^{-1}$, $MNC^{-2}$, and $MNC^{-3}$ were used. The value of MNC is given in Table 1.

In each trial, the following controls were set:
(i) cell control—only cells in culture medium and not infected with the virus; and
(ii) viral control—one column to cells infected with the virus were added only medium (200 μl) without the test compound 1 or the control compound 2.

Replication of HIV-1 in cell culture was measured by the MTT assay in addition, by recording the RT activity in the culture medium (fluid). This test shows the effect on the process of reverse transcription in the virus under appropriate experimental condition.

The activity of compound 1 or control compound 2 against the cytopathic effect of HIV-1 was expressed as percentage (%) protection (survival) of the cells defined by the following formula:

$$\% \text{ protection} = \frac{OD_{VS} - OD_{VC}}{OD_{CC} - OD_{VC}} \times 100 \ (\%)$$

wherein:
$OD_{VS}$=absorption of cells infected and treated with compound 1 or 2
$OD_{VC}$=absorption of the virus-infected cells (virus control without compound 1 or 2), and
$OD_{CC}$=absorption of uninfected cells (cell control)

The inhibitory concentration 50% ($IC_{50}$) was defined as the concentration of test compound 1 or control compound 2, expressed in mM, which inhibits 50% viral replication. $IC_{50}$ was determined directly from the curve "dose (concentration)—response (anti-HIV effect)". The $IC_{50}$ was expressed as percentage (%) of:

(i) cell viability which was obtained by the MTT assay; or
(ii) percentage (%) inhibition of enzyme reverse transcriptase (RT) activity.

On the basic of the data about $CC_{50}$ and $IC_{50}$ for the test substance 1 or control substance 2, the selectivity index (SI) value was estimated.

The study of the effects of any potential anti-HIV active substance starts always with the biological activity of the substance on the virus, without taking into account the mechanism or target of this effect. The impact of substance 1 or control compound 2 on the replication of HIV-1 was tested on cell line MT-4 my MTT assay for recording the cytopathic effect under the action of the virus. In fact, the test reported survival rates of cells infected with the virus and treated with different concentrations of test substance 1 or control substance 2. The expectation is that in the antiviral effect, the cells will be protected from the cytopathic effect of the virus compared to the virus control.

In all cases, we made a comparison with the survival of cells not infected with virus and without the addition of inhibitors (cell control), and cells infected with the virus, without the addition of inhibitors (virus control).

Therefore, in each experiment antiviral effect existed following obligatory statements:

(i) cells not treated with virus and substances (control cells);
(ii) cells treated with the virus, without addition of the test substance 1 or control substance 2 (control virus); and
(iii) cells infected with a virus, in which the culture medium after inoculation was added to the appropriate concentration of the test substance 1 or control substance 2.

The results of the experiments are given in Tables 2 and 3.

TABLE 2

Survival (% protection) of the MT-4 cells infected with HIV-1 under the action of 7,9-dihydroxy-3-(4,5,7-trihydroxy-2-oxo-2H-chromene-3-yl)-4H-furo[3,2-c]chromen-4-one (1) or 7,8-dihydroxy-3-(4,6,7-trihydroxy-2-oxo-2H-chromen-3-yl)-4H-furo[3,2-c]chromen-4-one (2) of previously determined MNC = 0.01 mM.

| No. | Concentration [mM] | Survival (% protection) | |
|---|---|---|---|
| | | Control compound 2 (state-of-the art) | Compound 1 (this invention) |
| 1 | 5 | —[a] | —[a] |
| 2 | 1 | —[a] | —[a] |
| 3 | 0.1 | —[a] | —[a] |
| 4 | 0.01 | 55 | 92 |
| 5 | 0.005 | 50 | 75 |
| 6 | 0.001 | 25 | 60 |
| 7 | 0.0001 | 0 | 55 |
| 8 | 0.00001 | 0 | 50 |
| 9 | 0.000001 | 0 | 0 |

[a]The corresponding concentrations were cytotoxic, therefore, the experiments at these concentrations were not pereformed.

The results from Table 2 show the survival (protection) of MT-4 cells after infection with HIV-1 and treated with the test compound 1 and control compound 2 at various concentrations of MNC. Thus was determined not only the biological activity of compounds 1 and 2, but also the $IC_{50}$ for both compounds by the MTT test. Based on data "dose—anti-HIV effect", the values of $IC_{50}$ of the test compound 1 and control compound 2 were determined (Table 3).

TABLE 3

Comparison of protection of MT-4 cells (% survival) in MNC, $CC_{50}$, $IC_{50}$, and SI of 7,9-dihydroxy-3-(4,5,7-trihydroxy-2-oxo-2H-chromene-3-yl)-4H-furo[3,2-c]chromen-4-one (1) and 7,8-dihydroxy-3-(4,6,7-trihydroxy-2-oxo-2H-chromen-3-yl)-4H-furo[3,2-c]chromen-4-one (2) in MT-4 cells infected with HIV-1 according to the MTT assay.

| No. | Parameter | Compound 2 (state-of-the-art) | Compound 1 (this invention) |
|---|---|---|---|
| 1 | MNC [mM] | 0.01 | 0.01 |
| 2 | % protection of the MT-4 cells in MNC | | 100 |
| 3 | $CC_{50}$ [mM] | 10 | 10 |
| 4 | $IC_{50}$ [mM] | 0.005 | 0.00001 |
| 5 | SI = $CC_{50}/IC_{50}$ | $2 \cdot 10^3$ | $1000 \cdot 10^3$ |

In comparison of the effect of the concentration of MNC and $IC_{50}$ shows that compound 1 protects the cells in high degree in MNC, 92%. It protects the cells of 60% even at a concentration 10 times (10×) lower than is the MNC.

In contrast, the control compound 2 from the prior art showed significantly lower antiviral activity, providing only 55% protection of the cells versus 92% observed for the compound 1 from this invention. Moreover even at 100× lower concentration (0.0001 mM) than is MNC, the prior art control compound 2 showed 0% of cell protection activity, in comparison with 55% which gave the compound 1 from this invention.

At all concentrations of compounds 1 or 2, dose-dependent reduction of cell survival in varying degrees was observed. This indicates that, reduction of the concentration of compound 1 or 2 decreases the survival rate of the cells, because then cytopathic effect of the virus increased.

In conclusion, the test compound 1 protects the cells with significantly stronger antiviral activity than the control compound 2 from the prior art.

Detailed experimental procedure of study of antiviral activity of compounds 1 and 2 is given in Example 5.

Study of Antiviral Activity of 7,9-dihydroxy-3-(4,5,7-trihydroxy-2-oxo-2H-chromene-3-yl)-4H-furo[3,2-c]chromen-4-one (1) via Study of Reverse Transcriptase (RT) Activity and Comparison with Literature Analogue 2

Furthermore, antiviral activity of compound 1 was studied on reverse transcriptase (RT) activity to elucidate potential mechanism of its antiviral action. This was done by using MT-4 cell line which was not infected with HIV-1. Source of HIV-1 culture fluid was chronically infected and producing HIV-1 subtype B cell line H9/HTLV III B.

Reverse transcriptase (RT) activity was determined:
(a) in the culture fluid of infected HIV-1 MT-4 cells at 72 hours after their infection (viral control);
(b) in the culture fluid of non-infected with HIV-1 cells at 72 hours and culturing without the addition of any substance (cell control); and
(c) in the culture fluid infected with HIV-1 MT-4 cells at 72 hours after infecting them, in which the desired concentration of the test compound 1 or the control compound 2 to the growth medium was added.

RT activity was determined according to the instructions of the producer. Separately was reported RT activity of standard recombinant reverse transcriptase (rRT), available in every kit. It was prepared 12-fold dilutions of the standard rRT. The manufacturer provides data on the amount of rRT in pg/well and pg/ml for each 12-fold dilution. The method used represents colorimetric method for non-radioactive determination of RT activity. It includes two stages:
(1) the synthesis of reverse transcript at the 3- or 24-hours incubation at 33° C. (which was determined experimentally); and
(2) quantitative determination of the resulting product.

In the synthesis of DNA using bromine deoxyuridine triphosphate (Brd UTP), which enter into the composition of the reaction mixture. It is included in the structure of the matrix/primer making up the DNA chain. Determination of incorporated Brd UTP was done by tracer-antibody Brd UTP, conjugated to the enzyme alkaline phosphatase. Followed colorimetrically determining the absorbance at A405 nm, which is proportional to the RT activity in the sample. According to the manufacturer, RT activity was considered positive when A405 values for the sample exceeded at least 2 times the values of A405 for negative control. Otherwise the sample was reported as such lacking RT activity, i.e. negative. The test was done by comparing the RT activity in the virus controls (100%) reported with viral RT activity in the wells treated with the test substance in the different concentrations in strict absence of RT activity in control cells. Percent inhibition of replication using the RT test was expressed as the difference between 100% (positive viral control without inhibitor) and % reported RT activity in the wells treated with the inhibitor (compounds 1 or 2) at various concentrations.

The RT test was performed by using HS-Lenti RT activity kit test provided by Cavidi (Sweden) for direct study of inhibitory effect of rRT. HS-Lenti RT activity assay provides an opportunity for direct determination of the effects of the test compound 1 and the control compound 2 on the activity of rRT, of known concentrations. This was achieved at the incubation mixture to determine RT activity by including the test or the control substance in dilutions desired, which showed activity in the preliminary study. Such opportunity is provided by the test kit manufacturer, see literature reference 10:

10) X. Shao, D. Ekstrand, R. Bhikhabhai, C. Kallander, J. Gronowitz: A non-radioactive microtitre plate reverse transcriptase (RT) assay, based on immobilized template, for screening of RT activity inhibitors and evaluation of the mode of action, *Antiviral Chem. Chemother.* 8 (1997) 149-159.

Detailed experimental procedure for study of effect of compounds 1 and 2 on reverse transcriptase (RT) activity is described in Example 6.

The measurement of RT activity is a widespread method for the quantitative determination of retroviruses replication. In the experimental set-up, primarily endogenous activity in supernatants was measured, i.e. in the culture fluid of virus infected cells and treated/untreated with inhibitor at 72 hours after cultivation.

For the control, commonly used substance with proven antiviral activity was employed; in our case, we used Kivexa, which contains 600 mg Abacavir and 300 mg of Lamivudine, which is applied in clinical practice as nucleoside inhibitor of RT. In the presence of RT inhibition in the test, it is concluded that not only the replication of the virus is inhibited, but also probably the target of the inhibitory effect is RT itself. To confirm this conclusion, it is necessary that percentage (%) of inhibition of the RT coincides with the % inhibition in the microtiter MTT assay. To prove this definitively, manufacturing company offers a test and for exogenous RT activity. Reaction mixture supplemented with inhibitor was prepared at desired concentration for the assay, and then, to the mixture, recombinant RT was added with a known activity and concentration. After incubation, we determined whether the activity of the enzyme shall be amended (inhibited) by action of the compounds 1 or 2. Table 4 shows the effects of different concentrations of tested compound 1 and control compound 2 on the replication of HIV-1 by measuring the endogenous and exogenous RT activity.

TABLE 4

Effect of different concentrations (column 3) of Kivexa (Abacavir + Lamivudine), 7,9-dihydroxy-3-(4,5,7-trihydroxy-2-oxo-2H-chromene-3-yl)-4H-furo[3,2-c]chromen-4-one (1) and 7,8-dihydroxy-3-(4,6,7-trihydroxy-2-oxo-2H-chromen-3-yl)-4H-furo[3,2-c]chromen-4-one (2) on the replication of HIV-1 in the infected MT-4 cells. The effect is measured by RT activity in the culture liquid (endogenous RT) (column 4), and by direct impact on rRT (exogenous recombinant RT; column 5).

| No. | Compound | Concentration (mM) | RT A405RT/ RT control A405, (%) inhibition$^a$ | rRT A405RT/ rRT control A405, (%) inhibition$^b$ |
|---|---|---|---|---|
| 1 | Kivexa (Abacavir + Lamivudine) | 0.01 | 100 | n.a. |
| | | 0.005 | 70 | n.a. |
| | | 0.0001 | 59 | n.a. |
| | | 0.00001 | 25 | n.a. |
| 2 | Compound 2 (state-of-the-art) | 0.01 | 0.437/1.000 (56.3) | 3.145/2.964 (0) |
| | | 0.005 | 0.490/1.000 (51) | —$^c$ |
| | | 0.001 | 0.743/1.000 (25.7) | —$^c$ |
| | | 0.0001 | 0.994/1.000 (0) | —$^c$ |
| 3 | Compound 1 (this invention) | 0.01 | 0.110/1.000 (89) | 0.805/2.964 (72.85) |
| | | 0.005 | 0.234/1.000 (76.6) | 2.980/2.964 (0) |

TABLE 4-continued

Effect of different concentrations (column 3) of Kivexa (Abacavir + Lamivudine), 7,9-dihydroxy-3-(4,5,7-trihydroxy-2-oxo-2H-chromene-3-yl)-4H-furo[3,2-c]chromen-4-one (1) and 7,8-dihydroxy-3-(4,6,7-trihydroxy-2-oxo-2H-chromen-3-yl)-4H-furo[3,2-c]chromen-4-one (2) on the replication of HIV-1 in the infected MT-4 cells. The effect is measured by RT activity in the culture liquid (endogenous RT) (column 4), and by direct impact on rRT (exogenous recombinant RT; column 5).

| No. | Compound | Concentration (mM) | RT A405RT/ RT control A405, (%) inhibition$^a$ | rRT A405RT/ rRT control A405, (%) inhibition$^b$ |
|---|---|---|---|---|
| | | 0.0001 | 0.450/1.000 (55) | —$^c$ |
| | | 0.00001 | 0.493/1.000 (50.7) | —$^c$ |
| | | 0.000001 | 0.987/1.000 (1.3) | —$^c$ |

Kivexa (600 mg of Abacavir + 300 mg of Lamivudine) = a reference RT inhibitor.
n.a. = not analysed; because of the lack of Abacavir triphosphate.
$^a$Negative control of the test for endogenous RT activity was A405 = 0.212. The positive control was A405 = 1.000. The experimental results were the average of 3-6 wells; these were selected in a manner that the extinctions in the MTT assay (A540) do not differ for more than 10%.
$^b$Negative control of the test for rRT activity was A405 = 0.232. The positive control for the test was rRT A405 = 2.964.
$^c$These were not analysed due to the strength of the results in the previous dilutions.

It is crucial that if the substance is nucleoside inhibitor of RT, to perform the activity, phosphorylation of cell kinases is required. The latter is not possible in the "cell-free" system, i.e. in the execution of the exogenous RT reaction. The last would be possible only in the case of working with triphosphates of the test substance. For this reason, exogenous RT for Abacavir was not carried out. However, this is only applied to nucleoside analogues and not for test compounds 1 or 2.

Compound 1 inhibits >89% HIV-1 infectivity in MT-4 cells (Table 4), which is consistent with the inhibition of RT in supernatants (endogenous RT). Similar situation is against rRT, which is slightly lower compared to the inhibition of endogenous RT.

From this study, one can conclude that the compound 1 from this invention showed a strong antiviral activity through inhibition of RT, whilst the control compound 2 from the prior art is minor or totally inactive (either endogenous or exogenous) RT inhibitor. In this manner, an antiviral activity of the prior art control compound 2 as observed earlier is probably not based on RT inhibition.

The RT inhibitory activity of the compound 1 is similar or slightly stronger than for the known antiviral agent Kivexa (Abacavir+Lamivudine).

Thus antiviral activity of compound 1 does target the reverse transcriptase (RT) of human immune deficiency virus-1 (HIV-1), despite the fact that inhibition against rRT is slightly lower, in comparison with the inhibition of endogenous RT.

Study of antiviral activity of 7,9-dihydroxy-3-(4,5,7-trihydroxy-2-oxo-2H-chromene-3-yl)-4H-furo[3,2-c]chromen-4-one (1) via Determination of Viral Load by FDA Approved Test and Comparison with Literature Analogue 2

The preparation of the MT-4 cell line and HIV-1 culture was the same as in previously described studies. Monitoring of the amount of virions during anti-viral analysis by measuring of the viral load with FDA approved test was performed as follows: The study was conducted with Real-Time polymerase chain reaction (PCR) test for in vitro quantitative assay of HIV-I with automated system Abbott Molecular's m2000, approved by the United States (US) Food and Drug Administration (FDA), and with the CE mark. Extraction of viral nucleic acid was carried out with an automatic extractor with magnetic particles—Abbott Molecular's m2000sp and Real-Time amplification; detection was performed with m2000rt. The sensitivity and range of the test was 40 (1.6 log copies/ml) to 10,000,000 (7.0 log copies/ml) copies/ml by the extraction of 1 ml of sample. The target region of the viral genome was a fragment of the integrase gene pol. The test was designed to detect HIV-1 subtypes A-H, group P and N. In every test sample, an internal control was placed.

The study included three controls: negative, low positive, and high positive with the following result:
(i) negative control—result negative (not detected);
(ii) low positive control—result 938 copies/ml (2.97 log) control levels; and
(iii) high positive control—result 92,927 copies/ml (4.97 log) control levels.

The controls were within the permissible range and the study was valid.

Beside the viral and cell controls, two samples were tested:
(1) viral control: MT-4 cells infected with HIV-1 culture fluid derived from chronically infected and producing HIV-1 subtype B cell line. The flask with infected cells was incubated for 5 days (120 h) at 37° C. and 5% content of $CO_2$. After expiry of the incubation period, the supernatant was collected and frozen at −70° C. to the study;
(2) cell control: only MT-4 cells in culture medium and not infected with a HIV-1;
(3) sample 1: acute infected MT-4 cells with HIV-1 and treated with the control compound 2 from the prior art, at maximal nontoxic concentration (MNC) of 0.01 mM; and
(4) sample 2: acute infected MT-4 cells with HIV-1 and treated with the compound 1 from the present invention, at maximal nontoxic concentration (MNC) of 0.01 mM.

Result from this study is given in Table 5. Experimental procedure for this study is described in Example 7.

TABLE 5

Comparison of antiviral effects of 7,9-dihydroxy-3-(4,5,7-trihydroxy-2-oxo-2H-chromene-3-yl)-4H-furo[3,2-c]chromen-4-one (1) and 7,8-dihydroxy-3-(4,6,7-trihydroxy-2-oxo-2H-chromen-3-yl)-4H-furo[3,2-c]chromen-4-one (2) against HIV-1 in MT-4 cell line by measuring of the viral load using FDA-approved test.

| No. | Sample | Viral load [copies/ml] (log) |
|---|---|---|
| 1 | Viral control | 4.897 (3.69 log) |
| 2 | Cell control | Negative (HIV RNA not detected) |
| 3 | Compound 2 (state-of-the-art) | 1.227 (3.09 log) |
| 4 | Compound 1 (this invention) | 1.016 (3.01 log) |

In this study, lower viral load against the result for the viral control means stronger antiviral activity. Compound 1 showed the lowest viral load, lower than is the result from the viral control run, what clearly indicates its antiviral activity. Moreover, the viral load obtained with compound 1 was significantly lower than was the viral load at the control compound 2 from the prior art, what proves stronger antiviral activity of the former versus the latter compound.

In conclusion, 7,9-dihydroxy-3-(4,5,7-trihydroxy-2-oxo-2H-chromene-3-yl)-4H-furo[3,2-c]chromen-4-one (1) is characterized by very low toxicity and very high antiviral activity.

This study shows the antiviral activity of the compound 1 from this invention is significantly stronger than that of the control compound 2 from the prior art (Tables 2, 3 and 5), and similar or slightly stronger than to those of known antiviral agent Kivexa based on fixed combination of active pharmaceutical ingredients Abacavir+Lamivudine (Table 4).

Tentative mechanism of antiviral action of compound 1 is based on inhibition of reverse transcriptase (RT) enzyme, but this might not be the only aspect of its antiviral action.

Use of the Composition from this Invention

Due to demonstrated profound antiviral activity of 7,9-dihydroxy-3-(4,5,7-trihydroxy-2-oxo-2H-chromene-3-yl)-4H-furo[3,2-c]chromen-4-one (1), the composition of the present invention that is derived from 1, in its various final dosage forms is used for treatment of various viral infections and virus-causing diseases.

The composition of the present invention can be used against the following viruses: enteroviruses A-J; rhinoviruses A-C; rotaviruses A-C; norovirus; influenza virus A-C and their several types like H1N1, H2N2, H3N2, H5N1, H7N7, H1N2, H9N2, H7N2, H7N3, H10N7, H7N9, and their other relatives; human papillomaviruses (HPV); polyomaviruses like John Cunningham virus (JCV) and Merkel cell virus (MCV); poxviruses; herpesviruses such as human simplex virus 1 (HSV-1), human simplex virus 2 (HSV-2), varicella zoster virus, Epstein-Barr virus (human herpesvirus 4; EBV/HHV-4), human cytomegalovirus (HHV-5), and Kaposi's sarcoma-associated herpesvirus (HHV-8); hepatitis A-C viruses (HAV, HBV, HCV); retroviruses like human immunodeficiency virus type 1 (HIV-1), type 2 (HIV-2) and their subtypes; SARS coronavirus; Ebola virus (EBOV); Marburg virus (MARV); Banna virus; rubella virus; measles virus; mumps virus; human parainfluenza viruses (hPIV 1-4); rabies virus; orbiviruses; as well as against other viruses that affect human or animal organism.

In this manner the composition of the present invention is used for treatment of diseases caused by above-mentioned viruses selected from the group comprising:
(i) non-cancer diseases: enteritis (enteroviruses A-J); common cold (rhinoviruses A-C); gastroenteritis, diarrhoea (rotaviruses A-E, norovirus); gastroenteritis (norovirus); influenza (influenza virus A-C); progressive multifocal leukoencephalopathy (JCV), nephrophathy, Merkel cell cancer (MCV), smallpox (variola) (poxvirus); herpes (HSV-1, HSV-2); chicken-pox, herpes zoster (shingles) (varicella zoster virus); infectious mononucleosis (HHV-4); hepatitis A (hepatitis A virus); hepatitis B (hepatitis B virus); hepatitis C (hepatitis C virus); acquired immunodeficiency syndrome (HIV-1, HIV-2, and their subtypes); severe acute respiratory syndrome (SARS); Ebola (EBOV); Marburg virus disease (MARV); fever and encephalitis (Banna virus); rubella (rubella virus); measles (measles virus); mumps (mumps virus); parainfluenza (hPIV 1-4); rabies (rabies virus);
(ii) virus-associated cancer diseases: Hodgkin's lymphoma, nasopharyngeal carcinoma, Burkitt's lymphoma (EBV/HHV-4); mucoepidermoid carcinoma (HHV-5); hepatocellular carcinoma (HBV, HCV); cancer of cervix, anus, penis, vagina, and oropharyngeal cancer (HPV); primary effusion lymphoma, Kaposi's sarcoma (HHV-8); as well as
(iii) autoimmune diseases often associated with various viruses: dermatomyositis, systemic lupus erythematosus, rheumatoid arthritis, multiple sclerosis, Sjögren's syndrome; and various other viral diseases of human and animals.

Depending on the kind of final dosage form, the composition of the present invention can be administered: orally, topically, parenterally, vaginally, rectally, via eyes, nose, or ears, or by inhalation. The therapy involves one or more administrations per day of pharmaceutically effective doses from 0.1-15 mg/kg of body weight, what represents 7.5-1.125 mg of active compound 1 per average adult person of 75 kg body weight.

EXAMPLES

General Remarks

Thin layer chromatography (TLC) was carried out on silica gel plates, Al-foil, 60HF$_{254}$, Merck, Darmstadt, Germany.

High performance liquid chromatography (HPLC) was performed on Agilent 1260 Infinity instrument.

Infrared (IR) spectra were recorded on Bruker Alpha FT-IR spectrometer with diamond-ATR sampling mode, and wave numbers (ν) are expressed in cm$^{-1}$.

NMR spectra were recorded on Bruker Avance III NMR spectrophotometer at 500 MHz ($^1$H) or 125 MHz ($^{13}$C). Chemical shifts (δ) were expressed in ppm against tetramethylsilane as an internal standard, whilst coupling constants are given in Hz.

Mass spectra were recorded on Agilent 6224 Accurate Mass TOE LC-MS system of the following characteristics: dual AP-ESI (electro-spray at atmospheric pressure) source; mass analyser for positive and negative ions of 25-20.000; mass resolution of >10.000 across whole mass area; accuracy >2 ppm.

Room temperature (r.t.) means the temperature interval of 20-25° C.

Studies of antiviral activities of the compound 1 from the present invention and the control compound 2 from the prior art were conducted in collaboration with Department of Virology of National Center of Infectious and Parasitic Diseases (NCIPD), Sofia, Bulgaria; Assist. Prof. Dr. P. Genova-Kalou, Dr. D. Pencheva, Assoc. Prof. dr. A. Tchorbanov, Assoc. Prof. Dr. I. Alexiev, and Prof. Dr. T. Kantardjiev.

Example 1

Synthesis of 7,9-dihydroxy-3-(4,5,7-trihydroxy-2-oxo-2H-chromen-3-yl)-4H-furo[3,2-c]chromen-4-one (1)

(a) Preparation of 4,5,7-trihydroxy-2H-chromen-2-one (6): To a 3-necked 3 l reaction flask, diethylether (900 ml) was added, followed by phloroglucinol (3; 126.00 g; 1 mol) and cyanoacetic acid (4; 85.00 g; 1 mol). The reaction mixture was intensively stirred with evolution of gaseous hydrogen chloride (HCl) for 6 hours with cooling and maintaining the temperature between 30-35° C. The reaction was carried out for 6 hrs. The mixture was then left overnight. The organic layer was decanted and residual product poured into a mixture of water (3 l) and ice (1 kg). Thus obtained suspension was stirred for 1 h and filtered on a Buchner funnel. The intermediate product is ketimide 5, which was further crystallized from 50% aqueous ethanol.

Thus purified ketimide 5 was hydrolysed in a mixture of 36% hydrochloric acid (1 l) and distilled water (500 ml) at reflux temperature (130° C.) for 90 minutes. Then, the reaction mixture was cooled to room temperature and obtained product in the form of precipitate was separated by filtration, and washed with water (3×100 ml). Crude product was dried on vacuum oven (60° C., overnight) and purified by crystallization from water-ethanol 9:1, V/V. Isolated product was dried in vacuum oven at 60° C. overnight yielding 174.60 g (90%) of pure compound 6 in the form of yellow crystals, m.p. 325° C. (dec.).

Single spot on TLC, $R_f$=0.40; benzene/methanol/ethyl acetate=3:4:5, V/V/V.

MS m/z: 193.03 [M−H$^+$]; M$_r$(5)=194.02.

FT-IR (KBr) ν (cm$^-$): 3502, 3411, 3258, 3082, 2631, 1608, 1565, 1470, 1426, 1358, 1296, 1266, 1211, 1160, 1075, 806.

$^1$H-NMR (DMSO-d$_6$) δ (ppm): 5.90 (s, 1H, H-6), 6.05 (s, 1H, H-8), 6.10 (s, 1H, H-3), 10.50 (s, 3H, 4,5,7-OH).

$^{13}$C-NMR (DMSO-d$_6$) δ (ppm): 89.9, 96.0, 97.2, 102.0, 155.0, 157.1, 159.0, 162.0, 168.0.

(b) Preparation of 7,9-dihydroxy-3-(4,5,7-trihydroxy-2-oxo-2H-chromene-3-yl)-4H-furo[3,2-c]chromen-4-one (1): To a 3-necked flask (250 ml), aceton (75 ml), 4,5,7-trihydroxy-2-oxo-2H-chromen-2-one (6; 4.74 g; 0.022 mol), and glyoxal (7; 0.93 ml of 40% solution) were added. The reaction mixture was heated under reflux (56° C.) for 1 h. Then, the reaction mixture was evaporated to dryness. The crude product (3.07 g) was triturated in a refluxing mixture of benzene/methanol/ethyl acetate (30 ml; 3:4:5, V/V/V), separated by filtration, washed with the same solvent mixture, and dried in vacuum oven at 40° C. overnight. Thus obtained product 1 was in the form of pale brown powderous crystals (2.95 g; 72%), m.p.>300° C. (dec.).

MS m/z: 409.08 [M−H$^+$]; M$_r$(1)=410.29.

FT-IR (KBr) ν (cm$^{-1}$): 3163, 3088, 2680, 2642, 1604, 1578, 1473, 1406, 1364, 1334, 1287, 1149, 1080, 829.

$^1$H-NMR (DMSO-d$_6$) δ (ppm): 6.12 (d, 1H, J=2.2 Hz), 6.14 (d, 1H, J=2.1 Hz), 6.32 (d, 1H, J=2.1 Hz), 6.35 (d, 1H, J=2.1 Hz), 6.89 (s, 1H), 10.6 (bs, 5H).

$^{13}$C-NMR (DMSO-d$_6$) δ (ppm): 88.6, 91.3, 93.1, 95.1, 97.1, 97.3, 98.4, 105.1, 108.4, 150.4, 153.8, 154.0, 154.6, 155.7, 157.3, 158.6, 159.5, 160.1, 161.5, 170.1.

Example 2

Analytics of 7,9-dihydroxy-3-(4,5,7-trihydroxy-2-oxo-2H-chromene-3-yl)-4H-furo[3,2-c]chromen-4-one (1)

Thin layer chromatography (TLC) method for analysis of compound 1: silica gel Al-foil plates Merck 60HF$_{254}$ (Darmstadt, Germany); eluent: benzene/methanol/ethyl acetate=3:4:5, V/V/V; visualization of the spot was performed under UV lamp at 254 nm; $R_f$(1)=0.12.

High performance liquid chromatography (HPLC) method for analysis of compound 1: column: ZORBAX Extend C18, 2.1×50 mm, 1.8 μm; mobile phase: water (A): acetonitrile (B), gradient program: $t_0$=80% A+20% B, $t_{10\ min}$=10% A+90% B; column temperature: 40° C.; detection: is carried out by means of PDA detector at 206 nm; retention time, $t_R$(1)=1.20 min.

Example 3

Preparation of monosodium salt of 7,9-dihydroxy-3-(4,5,7-trihydroxy-2-oxo-2H-chromene-3-yl)-4H-furo[3,2-c]chromen-4-one (1)

To 96% ethanol (100 ml), powderous compound 1 (1.00 g; 2.44 mmol) was added and stirred at room temperature for 15 minutes. Then, sodium hydroxide (0.10 g; 2.44 mmol; 1 equiv.) was added and stirred under inert atmosphere of nitrogen ($N_2$) for 1 h. Thus obtained reaction mixture was evaporated to dryness, and further dried at 60° C. in deep vacuum for 20 h. Thus obtained product (1.05 g; quant.) was monosodium salt of compound 1 in the form of odourless fine powder.

Example 4

Study of cytotoxicity of 7,9-dihydroxy-3-(4,5,7-trihydroxy-2-oxo-2H-chromene-3-yl)-4H-furo[3,2-c]chromen-4-one (1) on model MT-4 cell culture and comparison with the control compound 2 from the prior art Cytotoxicity of compound 1 and control compound 2 was determined through the study of cell growth and viability by the methods of determination of maximal non-toxic concentration (MNC) and concentration required for cell viability by 50% ($CC_{50}$).

The study of cytotoxicity of compounds 1 and 2 was performed on MT-4 cell line of human origin; a cell line transformed with the human T-cell lymphotropic virus-1 (HTLV-1).

The cells in the suspension culture are growing in clusters. They were cultivated in Roswell Park Memorial Institute (RPMI) growth medium, of type RPMI 1640 (Sigma-Aldrich, USA) supplemented with 15% fetal bovine serum (FBS; Sigma-Aldrich, USA), 100 U/ml penicillin G sodium (Sigma-Aldrich, USA), and 100 µg/ml streptomycin sulphate (Sigma-Aldrich, USA). Cells were passaged 1:3-1:5 at a density around $6-8 \cdot 10^4$ cells/ml, while the passage was re-suspended repeatedly.

Cell viability was estimated by a modification of the 3-(4,5-dimethylthiazol-2-yl)-2,5-diphenyltetrazolium bromide (MTT) assay, which is described in the reference 9.

The MTT reduction assay was one of the most frequently used methods for measuring cell proliferation and cytotoxicity. The intensity of colour, measured spectrophotometrically, of the MTT formazan produced by living, metabolically active cells by measuring the activity of succinate dehydrogenase, mostly located in mitochondria was proportional to the number of live cells present.

MTT is a yellow water soluble tetrazolium dye that is reduced by live, but not dead, cells to a purple formazan product that is insoluble in aqueous solutions.

Since the cell culture we have worked with were suspension, a solution of poly-L-lysine (PLL; $M_w$=90,000; Sigma-Aldrich, USA) was used for cell attachment on the bottom of a 96-well plate. The plates were treated with 100 µl of PLL at a concentration of 50 µg/ml in phosphate buffered saline (PBS; Sigma-Aldrich, USA), pH=7.4, then incubated for 1 h at room temperature. Followed aspiration of PLL solution and washing the plate twice with sterile PBS. Cells were then seeded at a concentration of $7-8 \cdot 10^4$ cells/100 µl for all experiments. Since the final volume of the culture medium in each well was 200 µl, additional 100 µl of 10% FBS (containing no cells) was added. For the purpose of the experiment, there was no need of forming a dense cell monolayer and after 24 h, when the adherent cells were stick to the plastic, the supernatant was decanted and adding 50 µl of previously prepared dilution of test compound. The well was completed with culture medium (150 µl) to a final volume of 200 µl. The plate was incubated at 37° C. and 5% content of $CO_2$ for 3 days (72 h). Cells grown in medium without the test compound served as a control.

After 72 h incubation, the medium was replaced with MTT (Sigma Aldrich, USA) and dissolved at a final concentration of 5 mg/ml in serum-free medium, for further 3 h incubation. Then, the MTT-formazan product was solubilised in ethanol/dimethyl sulfoxide (DMSO; Sigma-Aldrich, USA) (1:1, V/V), and the optical density was measured at a test wavelength of 540 nm. Each experiment was performed in triplicate.

Cell viability was reported as the percentage (%) of viable cells in the wells treated with different concentrations of the test substance compared to the control cells untreated with the substances. Maximal non-toxic concentration (MNC) and cytotoxic concentration for 50% of cells ($CC_{50}$) were calculated from the constructed "dose cellular survival" curve.

Both MNC and $CC_{50}$ values were evaluated simultaneously by morphological and by cell survival criteria. We used MTT-test, determining the living and early apoptotic cells. When microscopic observation of the morphology of the monolayer were carried out at 72 h after the treatment with test compound 1 and control compound 2 solutions in concentration range from 10 mM to 0.01 mM, typical cytopathology characterizing toxic effects were not registered. We found some morphology changes in comparison with the cell control only in treated wells with highest concentration of 100 mM, whose impact could be due to the content of a diluent used (DMSO).

To evaluate whether this effect is due to the toxicity of the tested compound 1, control compound 2, or DMSO, mortgaging control of growth medium RPMI 1640 supplemented with 2% FBS and DMSO was tested. We conducted a test with the same concentration range as with compounds 1 and 2. The results show that the toxicity of DMSO in lower dilutions is extremely small and does not have a toxic effect on the cells of both lines.

Figure 2:
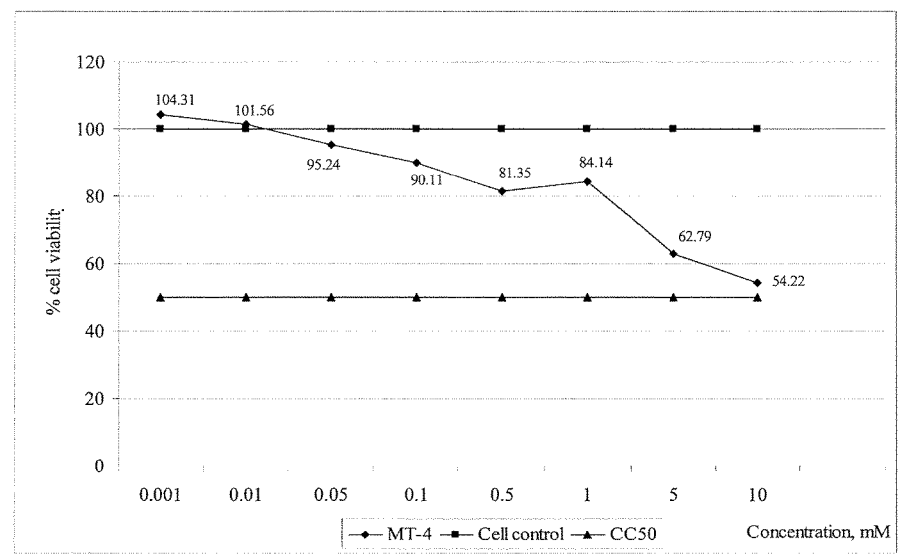
FIG. 2—Cytotoxic activity of control compound, 7,8-dihydroxy-3-(4,6,7-trihydroxy-2-oxo-2H-chromen-3-yl)-4H-furo[3,2-c]chromen-4-one (2), on viability of model MT-4 cell line. Dose - response curves obtained after 72 h culturing.

Cytotoxic activity of compounds 1 and 2 on viability of model MT-4 cell line can be seen from the dose—response curves obtained after 72 h culturing, see FIGS. 1 and 2.

The results of MNC and $CC_{50}$ obtained for both compounds 1 and 2 are given in Table 1.

Example 5

Study of antiviral activity of 7,9-dihydroxy-3-(4,5,7-trihydroxy-2-oxo-2H-chromene-3-yl)-4H-furo[3,2-c]chromen-4-one (1) and comparison with the control compound 2 from the prior art The compounds 1 or 2 were dissolved in dimethyl sulfoxide (DMSO; Sigma-Aldrich, USA) to a concentration of 1 mol/l (1 M) and after diluted in cell growth medium RPMI 1640 with 2% heat inactivated fetal bovine serum (FBS; Sigma-Aldrich, USA). All further solutions of compounds 1 or 2 were prepared ex tempore.

MT-4 cell line was not infected with HIV-1 and was used as a classic model for reproduction of acute infection with HIV-1. The cells were cultivated in RPMI 1640 growth medium supplemented with 15% fetal bovine serum (FBS; Sigma-Aldrich, USA), 100 U/ml penicillin G sodium (Sigma-Aldrich, USA), and 100 µg/ml streptomycin sulphate (Sigma-Aldrich, USA).

HIV-1 culture fluid was chronically infected and producing HIV-1 subtype B cell line H9/HTLV III B. The culture fluid was centrifuged and collected as a virus stock. The latter, used in the experiments, was of predetermined infectivity of $2 \cdot 10^6$ infectious virions/ml according to the microtiter infectivity assay based on the cytopathic effect of HIV, through ingestion of MTT, containing protein 24 antigen (p24) and enzyme reverse transcriptase (RT).

A microplate assay of infectivity in cell culture, based on consideration of a cytopathic effect of the virus was described in the literature, see reference 8.

After counting the cells, they were resuspended in growth medium at a concentration of $6\cdot8\cdot10^4$ cells/100 µl. Followed screening of cell suspensions (100 µl/well of that above) into sterile 96-well plates pretreated with poly-L-lysine (PLL). Since the final volume of the culture medium in each well was 200 µl, additional 100 µl of 10% FBS (containing no cells) was added. At the end of rows and columns were not seeded cells, but only culture medium without FBS.

After 24 h, the supernatant was decanted and added in 50 µl HIV-1 in dilution $10^{-1}$. One or two columns were not infected, acting as the control cells. The plate was placed in an incubator at 37° C. and 5% content of $CO_2$, for 1 h. The virus was then removed and in one or two columns of infected cells were added 200 µl medium containing the appropriate concentration of the test substance 1 or the control substance 2. At least 4 different concentrations: 10×MNC, MNC, $MNC^{-1}$, $MNC^{-2}$, and $MNC^{-3}$ were used. The value of MNC is given in Table 1.

In each trial, the following controls were set:
(i) a cell control—only cells in culture medium and not infected with the virus; and
(ii) a viral control—one column to cells infected with the virus were added only medium (200 µl) without the test substance 1 or the control substance 2.

For 5 days (120 h) the plates were incubated at 37° C. and 5% content of $CO_2$.

After expiry of the incubation period, the supernatant from each well was flipped in the well (mirror) of non-sterile 96-well plate. This was done in order to study only the supernatant from wells with parallel survival, e.g. indiscernible each other by more than ±10%, the same virus dilution/same concentration of the test substance. Subsequently, the MTT test was carried out as already described above.

In the living and early apoptotic cells after 4 h incubation from formazan crystals, which absorb light at wavelength of 540-570 nm. After accounting for the survival of the cells is determined separately from which wells of non-sterile 96-well plate to collect the supernatant for further research, e.g. determination of reverse transcriptase (RT) activity, culture medium was collected only from the wells with parallel survival, i.e. indiscernible each other by more than ±10%, the same virus dilution/same concentration of the test compound 1.

Replication of HIV-1 in cell culture was measured by the MTT assay in addition, by recording the RT activity in the culture medium (fluid). This test shows the effect on the process of reverse transcription in the virus under appropriate experimental condition.

The activity of the compound 1 or 2 against the cytopathic effect of HIV-1 was expressed as percentage (%) protection (survival) of the cells defined by the following formula:

$$\% \text{ protection} = \frac{OD_{VS} - OD_{VC}}{OD_{CC} - OD_{VC}} \times 100 \, (\%)$$

wherein:
$OD_{VS}$=absorption of cells infected and treated with compound 1 (or 2)
$OD_{VC}$=absorption of the virus-infected cells (virus control without compound 1 or 2)
$OD_{CC}$=absorption of uninfected cells (cell control)

The inhibitory concentration 50% ($IC_{50}$) was defined as the concentration of compound 1 (or 2), expressed in mM, which inhibits 50% viral replication. $IC_{50}$ was determined directly from the curve "dose (concentration)—response (anti-HIV effect)". The $IC_{50}$ was expressed as percentage (%) of:
(i) cell viability which was obtained by the MTT assay; or
(ii) percentage (%) inhibition of enzyme reverse transcriptase (RT) activity.

On the basic of the data about $CC_{50}$ and $IC_{50}$ for the test compound 1 and control compound 2, the selectivity index (SI) value was estimated.

The study of the effects of any potential anti-HIV active substance starts always with the biological activity of the substance on the virus, without taking into account the mechanism or target of this effect. The impact of compound 1 and control compound 2 on the replication of HIV-1 was tested on cell line MT-4 my MTT assay for recording the cytopathic effect under the action of the virus. In fact, the test reported survival rates of cells infected with the virus and treated with different concentrations of test substance 1 or the control substance 2. The expectation is that in the antiviral effect, the cells will be protected from the cytopathic effect of the virus compared to the virus control.

In all cases, we made a comparison with the survival of cells infected with virus and without the addition of inhibitors (cell control), and cells infected with the virus, without the addition of inhibitors (virus control).

The results of these experiments are given in Tables 2 and 3.

Example 6

Study of Antiviral Activity of 7,9-dihydroxy-3-(4,5,7-trihydroxy-2-oxo-2H-chromene-3-yl)-4H-furo[3,2-c]chromen-4-one (1) by Determination of Reverse Transcriptase (RT) Activity and Comparison with the Control Compound 2 from the Prior Art As described earlier, compound 1 or the control compound 2 were dissolved in dimethyl sulfoxide (DMSO; Sigma-Aldrich, USA) to a concentration of 1 mol/l (1 M) and after diluted in cell growth medium RPMI 1640 with 2% heat inactivated fetal bovine serum (FBS; Sigma-Aldrich, USA). All further solutions of compound 1 or 2 were prepared ex tempore.

This MT-4 cell line was not infected with HIV-1 and was used as a classic model for reproduction of acute infection with HIV-1. The cells were cultivated in RPMI 1640 growth medium (Sigma) supplemented with 15% fetal bovine serum (FBS; Sigma-Aldrich, USA), 100 U/ml penicillin G sodium (Sigma-Aldrich, USA), and 100 µg/ml streptomycin sulphate (Sigma-Aldrich, USA). As the cell lines which are working was suspension, we used a solution of poly-L-lysine (PLL; $M_w$=90,000; Sigma-Aldrich, USA) to attach them onto the bottom of a 96-well plate. The plate was dropped with 100 µl of PLL at concentration 50 µg/ml at PBS, followed by incubation for 1 h at room temperature. After withdrawal of the PLL solution, the plate was washed twice with sterile PBS. Thus treated plate was stored at +4° C. until use.

HIV-1: Source of HIV-1 culture fluid was chronically infected and producing HIV-1 subtype B cell line H9/HTLV III B. The culture fluid was centrifuged and collected as a virus stock. The latter used in the experiments was of a predetermined infectivity of $2\cdot10^6$ infectious virions/ml according to the microtiter infectivity assay based on the cytopathic effect of HIV through ingestion of MTT assay, see literature references 8 and 9.

Reverse transcriptase (RT) activity was determined:
(a) in the culture fluid of infected HIV-1 MT-4 cells at 72 hours after their infection (viral control);
(b) in the culture fluid of non-infected with HIV-1 cells at 72 hours and culturing without the addition of any substance (cell control); and
(c) in the culture fluid infected with HIV-1 MT-4 cells at 72 hours after infecting them, in which the desired concentration of the test compound 1 or the control compound 2 to the growth medium was added.

The culture fluids were collected in Eppendorf tubes and centrifuged at 10.000 rpm/min for 10 minutes, and then the supernatant was transferred to another Eppendorf tube, and stored at −70° C. until the time for determination of RT activity.

Centrifugation was carried out according to the manufacturer's instruction to eliminate even single cells into supernatant. RT activity was determined according to the instructions of the producer. Separately was reported RT activity of standard recombinant reverse transcriptase (rRT), available in every kit. It was prepared 12-fold dilutions of the standard rRT. The manufacturer provides data on the amount of rRT in pg/well and pg/ml for each 12-fold dilution. The method used represents colorimetric method for non-radioactive determination of RT activity. It includes two stages:
(1) the synthesis of reverse transcript at the 3- or 24-hours incubation at 33° C. (which was determined experimentally); and
(2) quantitative determination of the resulting product.

In the synthesis of DNA using bromine deoxyuridine triphosphate (Brd UTP), which enter into the composition of the reaction mixture. It is included in the structure of the matrix/primer making up the DNA chain. Determination of incorporated Brd UTP was done by tracer-antibody Brd UTP, conjugated to the enzyme alkaline phosphatase. Absorbance was followed colorimetrically at A405 nm. The later is proportional to the RT activity in the sample. According to the manufacturer, the RT activity was considered positive when A405 values for the sample exceeded at least 2 times the values of A405 for negative control. Otherwise the sample was reported as such lacking RT activity, i.e. negative. The test was done by comparing the RT activity in the virus controls (100%) reported with viral RT activity in the wells treated with the test substance in the different concentrations in strict absence of RT activity in control cells. Percent inhibition of replication using the RT test was expressed as the difference between 100% (positive viral control without inhibitor) and % reported RT activity in the wells treated with the inhibitor (compound 1 or 2) at various concentrations.

The RT test was performed by using HS-Lenti RT activity kit test for direct study of inhibitory effect of rRT, provided by Cavidi (Sweden; cat. no. 52010). HS-Lenti RT activity assay provides an opportunity for direct determination of the effects of the test compound 1 or the control compound 2 on the activity of rRT, which has a known concentration. This was achieved at the incubation mixture to determine the RT activity by including the test substance in dilutions desired, which showed activity in the preliminary study. Such opportunity is provided by the test kit manufacturer, see literature reference 10 for details.

The procedure was as follows: In wells of a company plate coated with a matrix poly-rA, are added reaction mixture to RT, the primer containing oligo-dT, Brd UTP as a source of dNTP and prepared at buffer of the commercial test 10× more concentrated (as reaction mixture was in a volume of 100 μl) of the test substance dilutions. Control was just a reaction mixture without active substance. After 30 minute incubation at 33° C., to each well rT standard of known concentration was added. In the subsequent incubation rRT manifests its activity by forming a product of the reverse transcription—RT-product. This was followed by washing and determination of the RT product by antibody against BrdU, conjugated with alkaline phosphatase for 90 minutes. Manifestation of the enzyme reaction was carried out using a suitable substrate for alkaline phosphatase for 30 minutes and then the absorbance was detected at a wavelength of 405 nm. In order to select the appropriate dilution of the recombinant enzyme, we prepared in advance twelve dilutions, and, on the basis of the results obtained, we built standard regression curve. We selected this dilution of the curve at which the absorption decreases in direct proportion to increase in the dilution of the recombinant enzyme; the area where the regression curve has a linear form.

Results: The measurement of RT activity is a widespread method for the quantitative determination of retroviruses replication. In the experimental set-up, primarily endogenous activity in supernatants was measured, i.e. in the culture fluid of virus infected cells, and treated/untreated with inhibitor at 72 hours after cultivation.

For the control, commonly used substance with proven antiviral activity was employed; in our case, we used Kivexa (600 mg Abacavir+300 mg Lamivudine), which is applied in clinical practice as nucleoside inhibitor of RT. In the presence of RT inhibition in the test, it is concluded that not only the replication of the virus is inhibited, but also probably the target of the inhibitory effect is RT itself. To confirm this conclusion, it is necessary that percentage (%) of inhibition of the RT coincides with the % inhibition in the microtiter MTT assay. To prove this definitively, manufacturing company offers a test and for exogenous RT activity. Reaction mixture supplemented with inhibitor was prepared at desired concentration for the assay, and then, to the mixture, recombinant RT was added with a known activity and concentration. After incubation, we determined whether the activity of the enzyme shall be amended (inhibited) by action of the compounds 1 and 2. Results are given in Table 4.

Example 7

Study of antiviral activity of 7,9-dihydroxy-3-(4,5,7-trihydroxy-2-oxo-2H-chromen-3-yl)-4H-furo[3,2-c]chromen-4-one (1) via Determination of Viral Load by FDA Approved Test and Comparison with the Control Compound 2 from the Prior Art The preparation of the MT-4 cell line and HIV-1 culture was the same as in previously described studies. The monitoring of the amount of virions during anti-viral analysis by measuring of the viral load with FDA approved test was performed as follows: The study was conducted with Real-Time polymerase chain reaction (PCR) test for in vitro quantitative assay of HIV-1 with automated system Abbott Molecular's m2000, approved by the United States (US) Food and Drug Administration (FDA), and with the CE mark. Extraction of viral nucleic acid was carried out with an automatic extractor with magnetic particles—Abbott Molecular's m2000sp and Real-Time amplification; detection was performed with m2000rt. The sensitivity and range of the test was 40 (1.6 log copies/ml) to 10,000,000 (7.0 log copies/ml) copies/ml by the extraction of 1 ml of sample.

The target region of the viral genome was a fragment of the integrase gene pol. The test was designed to detect HIV-1 subtypes A-H, group P and N. In every test sample, an internal control was placed.

The study included three controls: negative, low positive, and high positive with the following result:
(i) negative control—result negative (not detected);
(ii) low positive control—result 938 copies/ml (2.97 log) control levels; and
(iii) high positive control—result 92,927 copies/ml (4.97 log) control levels.

The controls were within the permissible range and the study was valid.

The following samples were tested:
(1) viral control: MT-4 cells infected with HIV-1 culture fluid derived from chronically infected and producing HIV-1 subtype B cell line. The flask with infected cells was incubated for 5 days (120 h) at 37° C. and 5% content of $CO_2$. After expiry of the incubation period, the supernatant was collected and frozen at −70° C. to the study;
(2) cell control: only MT-4 cells in culture medium and not infected with a HIV-1;
(3) sample 1: acute infected MT-4 cells with HIV-1 and treated with the control compound 2 from the prior art, at maximal nontoxic concentration (MNC) of 0.01 mM; and
(4) sample 2: acute infected MT-4 cells with HIV-1 and treated with the compound 1 from the present invention, at maximal nontoxic concentration (MNC) of 0.01 mM. Result from this study is given in Table 5.

Example 8

Preparation of the Composition from the Invention in the Dosage Form of Powder with 20% of 7,9-dihydroxy-3-(4,5,7-trihydroxy-2-oxo-2H-chromene-3-yl)-4H-furo[3,2-c]chromen-4-one (1)

Composition (for 100 g of powder):
(1) 20.00 g compound 1
(2) 1.00 g colloidal silicon dioxide
(3) 10.00 g xylitol
(4) 69.00 g maltodextrin Preparation: Previously weighted ingredients (1-4) were de-agglomerated and homogenized in V-blender for 15 minutes. The product was in the form of white off to pale brown fine free-flowing powder. Such powder can be granulated to yield granules of various sizes that can be employed as sole final dosage form.

Powder or granules is used either as a bulk form or as divided form, wherein the correct single dose is weighted and filled into suitable container, e.g. sachet.

Example 9

Preparation of the Composition from the Invention in the Dosage Form of Tablets with 100 mg of 7,9-dihydroxy-3-(4,5,7-trihydroxy-2-oxo-2H-chromene-3-yl)-4H-furo[3,2-c]chromen-4-one (1) Per Tablet Composition (for 1000 g of tablets):
(1) 100.00 g compound 1
(2) 6.00 g methyl cellulose
(3) 50.00 g cross-linked polyvinylpyrrolidone
(4) 15.00 g magnesium stearate
(5) 829.00 g lactose monohydrate
(6) q.s. purified water Preparation: Powderous compound 1 was homogenized with lactose monohydrate in V-blender for 15 minutes, subsequently granulated with aqueous solution of methyl cellulose. The wet mass was forced through a sieve and granulate dried in an oven. After drying, granulate was mixed with polyvinylpyrrolidone and magnesium stearate, and homogenized in V-blender for 15 minutes. The resulting mixture was pressed into tablet cores. Tablet content: 100 mg ±15% of compound 1 per tablet.

Example 10

Preparation of the Composition from the Invention in the Dosage Form of Capsules with 25 mg 7,9-dihydroxy-3-(4,5,7-trihydroxy-2-oxo-2H-chromene-3-yl)-4H-furo[3,2-c]chromen-4-one (1) Per Capsule Composition (for 1000 g of homogeneous mixture for capsules filling):
(1) 62.50 g compound 1
(2) 10.00 g magnesium stearate
(3) 927.50 g corn starch Preparation: Previously weighted ingredients (1-3) were de-agglomerated and homogenized in V-blender for 20 minutes. Thus obtained homogeneous powder was filled into vegetable (HPMC) colourless capsules of size 1 using manual capsule filling machine. Obtained capsules were of average weight of 400 mg. Capsule content: 25 mg ±15% of compound 1 per capsule.

Example 11

Preparation of the Composition from the Invention in the Dosage Form of Syrup-Suspension with 2% of 7,9-dihydroxy-3-(4,5,7-trihydroxy-2-oxo-2H-chromene-3-yl)-4H-furo[3,2-c]chromen-4-one (1)

Composition (for 100 g of syrup):
(1) 2.00 g compound 1
(2) 5.00 g glycerol
(3) 30.00 g saccharose
(4) 0.50 g potassium sorbate
(5) 0.25 g sodium benzoate
(6) 1.00 g citric acid, anhydrous
(7) 0.80 g xanthan gum
(8) 0.10 g lemon flavour
(9) 60.35 g purified water
(10) q.s. 1% aqueous solution of tartrazine yellow dye Preparation: Potassium sorbate, sodium benzoate, and glycerol were dissolved in purified water with stirring at room temperature for 10 minutes. Then, xanthan gum and saccharose was added, and dissolved with stirring at 40-50° C. for 15-20 minutes. Then, compound 1 was added and homogenized by stirring for 10 minutes. Afterwards, orange flavour, citric acid, and small amount of aqueous solution of tartrazine dye were added, and the resulting syrup was homogenized by stirring at 40° C. to room temperature for 30 minutes. The product was in the form of yellow viscous syrup-suspension of orange taste. It is declared with the mark: "shake well before use".

Example 12

Preparation of the composition from the invention in the dosage form of ointment with 3% w/w of 7,9-dihydroxy-3-(4,5,7-trihydroxy-2-oxo-2H-chromene-3-yl)-4H-furo[3,2-c]chromen-4-one (1)

Composition (for 100 g of ointment):
(1) 3.00 g compound 1
(2) 3.00 g lanolin alcohol (3) 2.00 g cetostearyl alcohol
(4) 20.00 g mineral oil, heavy
(5) 72.00 g petroleum jelly Preparation: Mixture of petroleum jelly, heavy mineral oil, lanolin and cetostearyl alcohol was melted at 50-55° C. with stirring until clear pale yellow liquid is obtained. Then, compound 1 was added, and homogenized by stirring with gradual cooling from 50° C. to 30-35° C. during 1 h, and filled at this temperature into 30 ml jars. Thus obtained ointment was in the form of pale yellow occlusive grease of slight odour after lanolin.

Example 13

Preparation of the composition from the invention in the dosage form of cream with 2% w/w of 7,9-dihydroxy-3-(4,5,7-trihydroxy-2-oxo-2H-chromene-3-yl)-4H-furo[3,2-c]chromen-4-one (1)

Composition (for 100 g of cream):
(1) 2.00 g compound 1
(2) 5.00 g 1,2-propylene glycol
(3) 4.00 g cetyl alcohol
(4) 4.00 g glyceryl monostearate
(5) 5.00 g polysorbate 60
(6) 5.00 g hexadecyl palmitate
(7) 10.00 g isopropyl myristate
(8) 0.25 g citric acid, anhydrous
(9) 0.50 g ammonium hydrogencitrate
(10) 0.20 g methyl 4-hydroxybenzoate (methylparaben)
(11) 0.10 g propyl 4-hydroxybenzoate (propylparaben)
(12) 63.95 g purified water Preparation: Oil phase was prepared by melting of isopropyl myristate, hexadecyl palmitate, polysorbate 60, glyceryl monostearate, and cetyl alcohol at 70-75° C. Aqueous phase was prepared by dissolving methyl and propyl parabens, citric acid, and ammonium hydrogencitrate in a mixture of purified water and 1,2-propylene glycol at 45-50° C. with stirring. Thus obtained solution was heated to 70-75° C. Then, hot aqueous phase (70-75° C.) was added dropwise with intensive stirring to the oil phase (70-75° C.) during 30 minutes. The mixture was stirred at 70-60° C. during 30 minutes and at 60-50° C. during additional 30 minutes. Thus obtained emulsion was further homogenized by stirring at 50° C. down to 25° C. during 1 h. The product was filled into suitable containers, e.g. jars or tubes. The product was in the form of almost odourless, light oil-in-water (O-W) cream.

Example 14

Preparation of the Composition from the Invention in the Dosage form of Suppositories with 100 mg 7,9-dihydroxy-3-(4,5,7-trihydroxy-2-oxo-2H-chromene-3-yl)-4H-furo[3,2-c]chromen-4-one (1) per suppository Composition (for 100 g of suppositories):
(1) 3.50 g compound 1
(2) 96.50 g hydrogenated coconut oil, type Witepsol H15

Preparation: Witepsol H15 was melted at 40-45° C. with stirring until colourless viscous liquid is obtained. Then, compound 1 was added and homogenized with stirring at 40-45° C. for 15 minutes. Thus obtained suspension was filled into PE HD suppository molds of type A3 (internal volume 3 mL), then cooled and sealed. The product was in the form of pale yellow hard suppositories. Analysis showed the content of 100 mg ±10 mg (10%) of compound 1 per suppository. These suppositories can be used for either vaginal or rectal application.

Example 15

Preparation of the Composition from the Present Invention in the Form of Liquid Nasal Spray with 0.01% of 7,9-dihydroxy-3-(4,5,7-trihydroxy-2-oxo-2H-chromene-3-yl)-4H-furo[3,2-c]chromen-4-one (1)

Composition (for 100 g of liquid for spray):
(1) 0.01 g compound 1
(2) 0.90 g sodium chloride
(3) 0.10 g sodium dihydrogenphosphate
(4) 0.05 g sodium hydrogenphosphate
(5) 0.05 g disodium edetate dihydrate
(6) 2.00 g glycerol
(7) 96.89 g purified water Preparation: Sodium chloride, sodium phosphates, disodium edetate dihydrate were added to a mixture of water and glycerol, and dissolved by stirring at room temperature for 15 minutes. Then, compound 1 was added and homogenized by stirring at r.t. for 30 minutes. Thus obtained solution was filtered through:
(1) the 1.2 μm polypropylene (PP) filter;
(2) 0.2 μm filter to reduce bioburden; and
(3) through 0.1 μm filter.

The product was in the form of pale yellow almost odourless liquid. Analysis showed the content of 0.1 mg/ml ±10% of compound 1. The solution was filled into 10 ml plastic (PE-HD) bottles with spraying device or alternatively into containers for nasal or oral (pulmonal) aerosols for administration by inhalation devices.

Conclusion

A. 7,9-Dihydroxy-3-(4,5,7-trihydroxy-2-oxo-2H-chromene-3-yl)-4H-furo[3,2-c]chromen-4-one (1) is a new, previously unknown compound that is characterized by a profound antiviral (HIV-1) activity:

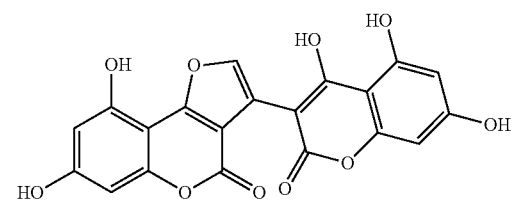

B. According to our best knowledge, the closest prior art structural analogue is 7,8-dihydroxy-3-(4,6,7-trihydroxy-2-oxo-2H-chromen-3-yl)-4H-furo[3,2-c]chromen-4-one (2), disclosed in the literature reference 6:

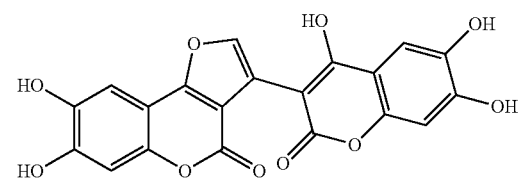

C. The present invention discloses experimental results that strongly support the claim that the compound 1 exhibits significantly stronger antiviral (HIV-1) activity than the control compound 2 from the prior art. This statement was proved by different anti-viral models:
  (a) determination of percentage (%) of cell protection against HIV-1 virus in MT-4 cell line; for results see Tables 2 and 3; and
  (b) antiviral analysis by measuring of the viral load with FDA approved test with Real-Time PCR test for in vitro quantitative assay of HIV-1; for results see Table 5.
  Moreover, the study of potential mechanism of antiviral action of compounds 1 and 2 (for results see Table 4), which was presumed to be via reverse transcriptase (RT) inhibition, showed that the compound 1 from this invention is a strong RT inhibitor, whilst the control compound 2 from the prior art is minor or totally inactive RT inhibitor.
D. In conclusion, the compound 1 from the present invention is characterized by stronger anti-viral (HIV-1) activity than the compound 2 from the prior art, which is also based on different mechanism in the same time. The antiviral activity of compound 1 might involves RT inhibition as predominant manner of its action.
  In this manner, these facts support the claim that the compound 1 from the present invention is unexpectedly more effective antiviral agent than is the control compound 2 from the closest prior art.
  Therefore the compound 1, process for its preparation, pharmaceutical composition and use thereof are inventive.

INDUSTRIAL APPLICABILITY

Compound 7,9-Dihydroxy-3-(4,5,7-trihydroxy-2-oxo-2H-chromene-3-yl)-4H-furo[3,2-c]chromen-4-one (1) or a pharmaceutically acceptable salt or hydrate thereof is used as active pharmaceutical ingredient (API) for production the composition disclosed via present invention. Compositions are used in manufacturing of medicament for treatment of viral infections and virus-causing diseases, including the acquired immunodeficiency syndrome (AIDS) caused by the human immunodeficiency virus type 1 (HIV-1).

The invention claimed is:
1. A compound of formula (1)

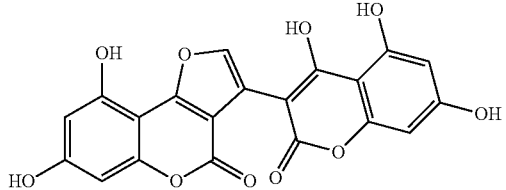

(1)

or a pharmaceutically acceptable salt or hydrate thereof.
2. The compound according to claim 1 for use in a therapy of viral infections and virus-causing diseases of human and animals.
3. The compound according to claim 2 where the viral infection and virus-causing disease is caused by one or more viruses selected from the group consisting of: enteroviruses A-J; rhinoviruses A-C; rotaviruses A-C; norovirus; influenza virus A-C and their types selected from the group consisting of H1N1, H2N2, H3N2, H5N1, H7N7, H1N2, H9N2, H7N2, H7N3, H10N7, or H7N9; human papillomaviruses; polyomaviruses: John Cunningham virus and Merkel cell virus; poxviruses; herpesviruses selected from the group consisting of human simplex virus 1, human simplex virus 2, varicella zoster virus, Epstein-Barr virus or human herpesvirus 4; human cytomegalovirus, and Kaposi's sarcoma-associated herpesvirus; hepatitis A-C viruses; SARS coronavirus; Ebola virus; Marburg virus; Banna virus; rubella virus; measles virus; mumps virus; human parainfluenza viruses; rabies virus and orbiviruses.
4. The compound according to claim 2 where the virus-causing disease is one selected from the following groups:
  (i) non-cancer diseases: enteritis, common cold, gastroenteritis, diarrhoea, gastroenteritis, influenza, progressive multifocal leukoencephalopathy, nephrophathy, Merkel cell cancer, smallpox, herpes, chicken-pox, herpes zoster, infectious mononucleosis, hepatitis A, hepatitis B, hepatitis C, severe acute respiratory syndrome, Ebola, Marburg virus disease, fever and encephalitis, rubella, measles, mumps, parainfluenza, rabies;
  (ii) virus-associated cancer diseases: Hodgkin's lymphoma, nasopharyngeal carcinoma, Burkitt's lymphoma, mucoepidermoid carcinoma, hepatocellular carcinoma; cancer of cervix, anus, penis, vagina, and oropharyngeal cancer; primary effusion lymphoma, Kaposi's sarcoma;
  (iii) autoimmune diseases associated with viruses selected from the group consisting of: dermatomyositis, systemic lupus erythematosus, rheumatoid arthritis, multiple sclerosis, or Sjögren's syndrome.
5. The compound according to claim 2 where the viral infection is human immunodeficiency virus infection.
6. The compound according to claim 2 the where viral infection is human immunodeficiency virus type 1 infection.
7. A pharmaceutical composition comprising:
  (1) the compound of claim 1 as active pharmaceutical ingredient; and
  (2) one or more pharmaceutical excipients.
8. The pharmaceutical composition according to claim 7 for use in a therapy of viral infections and virus-causing diseases of human and animals.
9. The pharmaceutical composition according to claim 8 where the viral infection and virus-causing disease is caused by one or more viruses selected from the group consisting of: enteroviruses A-J; rhinoviruses A-C; rotaviruses A-C; norovirus; influenza virus A-C and their types selected from the group consisting of H1N1, H2N2, H3N2, H5N1, H7N7, H1N2, H9N2, H7N2, H7N3, H10N7, or H7N9; human papillomaviruses; polyomaviruses: John Cunningham virus and Merkel cell virus; poxviruses; herpesviruses selected from the group consisting of human simplex virus 1, human simplex virus 2, varicella zoster virus, Epstein-Barr virus or human herpesvirus 4; human cytomegalovirus, and Kaposi's sarcoma-associated herpesvirus; hepatitis A-C viruses; SARS coronavirus; Ebola virus; Marburg virus; Banna virus; rubella virus; measles virus; mumps virus; human parainfluenza viruses; rabies virus and orbiviruses.
10. The pharmaceutical composition according to claim 8 where the virus-causing disease is one selected from the following groups:
  (i) non-cancer diseases: enteritis, common cold, gastroenteritis, diarrhoea, gastroenteritis, influenza, progressive multifocal leukoencephalopathy, nephrophathy, Merkel cell cancer, smallpox, herpes, chicken-pox, herpes zoster, infectious mononucleosis, hepatitis A, hepatitis B, hepatitis C, severe acute respiratory syndrome, Ebola, Marburg virus disease, fever and encephalitis, rubella, measles, mumps, parainfluenza, rabies;
(ii) virus-associated cancer diseases: Hodgkin's lymphoma, nasopharyngeal carcinoma, Burkitt's lymphoma, mucoepidermoid carcinoma, hepatocellular carcinoma; cancer of cervix, anus, penis, vagina, and oropharyngeal cancer; primary effusion lymphoma, Kaposi's sarcoma;
(iii) autoimmune diseases associated with viruses selected from the group consisting of: dermatomyositis, systemic lupus erythematosus, rheumatoid arthritis, multiple sclerosis, or Sjögren's syndrome.

11. The pharmaceutical composition according to claim 8 where the viral infection is human immunodeficiency virus infection.

12. The pharmaceutical composition according to claim 8 where the viral infection is human immunodeficiency virus type 1 infection.

13. A process for preparing the compound of claim 1, comprising the step of reacting 4,5,7-trihydroxy-2H-chromen-2-one with glyoxal in an inert reaction solvent at a temperature in the range of from −20° C. to +100° C. to yield the compound of formula (1).

14. The process of claim 13, wherein the inert reaction solvent is selected from the group consisting of acetone, tetrahydrofuran, 1,4-dioxan, diisopropylether, and dichloromethane.

15. The process of claim 14, wherein the inert reaction solvent is acetone and the temperature is 56° C.

\* \* \* \* \*

UNITED STATES PATENT AND TRADEMARK OFFICE
CERTIFICATE OF CORRECTION

PATENT NO. : 10,266,545 B2
APPLICATION NO. : 15/562081
DATED : April 23, 2019
INVENTOR(S) : Mladen Trkovnik, Milan Cacic and Jonuz Rizvani It is certified that error appears in the above-identified patent and that said Letters Patent is hereby corrected as shown below:

On the Title Page

(30) Foreign Application Priority Data, delete "Feb. 2, 2016 (WO) PCT/HR 2016/000005" and insert -- March 30, 2015 (HR) PCT/HR2015/000008 --.

Signed and Sealed this
Second Day of July, 2019

Andrei Iancu
*Director of the United States Patent and Trademark Office*